(12) United States Patent
Zhang et al.

(10) Patent No.: US 8,301,233 B2
(45) Date of Patent: Oct. 30, 2012

(54) DETECTING A CONDITION OF A PATIENT USING A PROBABILITY-CORRELATION BASED MODEL

(75) Inventors: Xusheng Zhang, Shoreview, MN (US); Robert W. Stadler, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 613 days.

(21) Appl. No.: 12/415,445

(22) Filed: Mar. 31, 2009

(65) Prior Publication Data

US 2010/0249627 A1    Sep. 30, 2010

(51) Int. Cl.
*A61B 5/02* (2006.01)
*A61B 5/08* (2006.01)

(52) U.S. Cl. .................. 600/515; 600/508; 600/518

(58) Field of Classification Search .......... 600/508–509, 600/513–518
See application file for complete search history.

(56) References Cited

U.S. PATENT DOCUMENTS

| | | | |
|---|---|---|---|
| 5,000,189 A | | 3/1991 | Throne et al. |
| 5,086,772 A | | 2/1992 | Larnard et al. |
| 5,379,776 A | | 1/1995 | Murphy et al. |
| 5,423,863 A | | 6/1995 | Felblinger et al. |
| 5,590,650 A | * | 1/1997 | Genova .......................... 600/301 |
| 5,873,897 A | | 2/1999 | Armstrong et al. |
| 6,064,906 A | * | 5/2000 | Langberg et al. .............. 600/518 |
| 6,110,109 A | * | 8/2000 | Hu et al. ........................ 600/300 |
| 6,272,377 B1 | * | 8/2001 | Sweeney et al. ............... 600/515 |
| 6,427,083 B1 | | 7/2002 | Owen et al. |
| 7,027,856 B2 | * | 4/2006 | Zhou et al. ..................... 600/515 |
| 7,076,290 B2 | | 7/2006 | Sheth et al. |
| 7,127,290 B2 | * | 10/2006 | Girouard et al. ................ 607/17 |
| 7,343,197 B2 | * | 3/2008 | Shusterman ................... 600/509 |
| 7,474,916 B2 | | 1/2009 | Gutierrez |
| 2004/0254613 A1 | | 12/2004 | Ostroff et al. |

(Continued)

FOREIGN PATENT DOCUMENTS

EP    0360412 A1    3/1990

(Continued)

OTHER PUBLICATIONS

P0029608.01 (PCT/US2010/027991) PCT Notification of Transmittal of the International Search Report and the Written Opinion of the International Searching Authority, dated Jun. 22, 2010, 7 pages.

*Primary Examiner* — Niketa Patel
*Assistant Examiner* — Catherine Voorhees
(74) *Attorney, Agent, or Firm* — Stephen W. Bauer; Michael J. Ostrom

(57) ABSTRACT

Techniques are described for detecting a condition of a patient using a probability-correlation based model that integrates a plurality of parameters associated with the condition. A medical device that operates in accordance with the techniques obtains a plurality of parameters associated with the condition of the patient. The medical device obtains probabilities that the condition of the patient exists based on each single parameter separately and correlations between each of the parameters and the other ones of the parameters. After obtaining the probabilities and correlations associated with each of the parameters, the medical device determines whether the condition of the patient exists based on the determined probabilities and correlations. Such techniques may be particularly effective for use in distinguishing whether a rhythm of a patient is treatable, e.g., VT or VF, or non-treatable, e.g., SVT.

17 Claims, 12 Drawing Sheets

U.S. PATENT DOCUMENTS

| | | |
|---|---|---|
| 2006/0025822 A1 | 2/2006 | Zhang |
| 2006/0155201 A1 | 7/2006 | Schwartz et al. |
| 2006/0247703 A1 | 11/2006 | Gutierrez |
| 2007/0191894 A1 | 8/2007 | Li |
| 2007/0232948 A1 | 10/2007 | Stadler et al. |
| 2007/0239051 A1 | 10/2007 | Ghanem et al. |
| 2007/0239220 A1 | 10/2007 | Greenhut et al. |
| 2007/0270704 A1 | 11/2007 | Ghanem et al. |
| 2008/0169813 A1 | 7/2008 | Yamashita et al. |
| 2008/0269624 A1 | 10/2008 | Zhang et al. |
| 2008/0269625 A1* | 10/2008 | Halperin et al. ............ 600/508 |

FOREIGN PATENT DOCUMENTS

| | | |
|---|---|---|
| EP | 1219237 A2 | 7/2002 |
| WO | 2003003905 | 1/2003 |
| WO | WO2005112749 | 12/2005 |
| WO | WO2008137529 | 11/2008 |

* cited by examiner

DETECTING A CONDITION OF A PATIENT USING A PROBABILITY-CORRELATION BASED MODEL

TECHNICAL FIELD

This disclosure relates to implantable medical devices (IMDs), and, more particularly, to classifying a condition of a patient using a probability-correlation based model.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter-defibrillators (ICDs), provide therapeutic electrical stimulation to or monitor the heart of the patient via electrodes carried by one or more implantable leads. The leads are typically implanted transvenous, i.e., implanted in the heart through one or more veins, sometimes referred to as endocardial leads. Other IMDs, sometimes referred to as subcutaneous devices, may include leads that are not implanted within the heart. Instead, these leads are implanted outside of the heart under the skin or on the outside of the heart (referred to as epicardial leads). In either case, the electrical stimulation provided by the IMD may include signals such as pacing pulses, cardiac resynchronization pulses, cardioversion shocks or defibrillation shocks to address abnormal cardiac rhythms such as bradycardia, tachycardia or fibrillation.

In some cases, the IMD may sense signals representative of intrinsic depolarizations of the heart and analyze the sensed signals to identify normal or abnormal rhythms. Upon detection of an abnormal rhythm, the device may deliver an appropriate electrical stimulation signal or signals to restore or maintain a more normal rhythm. For example, in some cases, an IMD may deliver pacing pulses to the heart upon detecting tachycardia or bradycardia, and deliver cardioversion or defibrillation shocks to the heart upon detecting tachycardia or fibrillation.

SUMMARY

In general, the disclosure is directed to techniques for detecting a condition of a patient using a probability-correlation based model that integrates a plurality of parameters associated with the condition. A medical device that operates in accordance with the techniques obtains a plurality of parameters associated with the condition of the patient. The medical device obtains probabilities that the condition of the patient exists based on each single parameter separately and correlations between each of the parameters and the other ones of the parameters. After obtaining the probabilities and correlations associated with each of the parameters, the medical device determines whether the condition of the patient exists based on the determined probabilities and correlations. Such techniques may be particularly effective for use in distinguishing whether a rhythm of a patient is treatable, e.g., VT or VF, or non-treatable, e.g., SVT.

In one example, the disclosure provides a method comprising obtaining a plurality of parameters associated with a condition of a patient, obtaining probabilities that the condition of the patient exists based on each of the plurality of parameters individually, obtaining correlations between each of the parameters and the other ones of the plurality of parameters, and determining whether the condition of the patient exists based at least on the probabilities and correlations.

In another example, the disclosure provides an implantable medical device comprising a sensing module configured to acquire at least one physiological signal of a patient via at least one sensor and a processor configured to analyze the acquired signal obtain a plurality of parameters associated with a condition of the patient, obtain probabilities that the condition of the patient exists based on each of the plurality of parameters individually, obtain correlations between each of the parameters and the other ones of the plurality of parameters, and determine whether the condition of the patient exists based at least on the probabilities and correlations.

In another example, the disclosure provides a computer-readable storage medium comprising instructions that, when executed by a processor in an implantable medical device, cause the processor to obtain a plurality of parameters associated with a rhythm of a heart of a patient, obtain probabilities that the rhythm is treatable based on each of the plurality of parameters individually, obtain correlations between each of the parameters and the other ones of the plurality of parameters, obtain independent contribution coefficients associated with each of parameters using the correlations, wherein the independent contribution coefficients represent the independent contribution of the particular parameter to the overall probability that the rhythm is treatable, determine an overall probability that the rhythm is treatable by multiplying each of the probabilities by the corresponding one of the independent contribution coefficients to obtain weighted probabilities and summing the weighted probabilities, and determine whether the rhythm is treatable based at least on the overall probability that the rhythm is treatable.

In a further example, the disclosure provides a medical device that includes means for obtaining a plurality of parameters associated with a condition of a patient, means for obtaining probabilities that the condition of the patient exists based on each of the plurality of parameters individually, means for obtaining correlations between each of the parameters and the other ones of the plurality of parameters, and means for determining whether the condition of the patient exists based at least on the probabilities and correlations.

The details of one or more aspects of the disclosure are set forth in the accompanying drawings and the description below. Other features, objects, and advantages will be apparent from the description and drawings, and from the claims.

DETAILED DESCRIPTION

Figure 1:
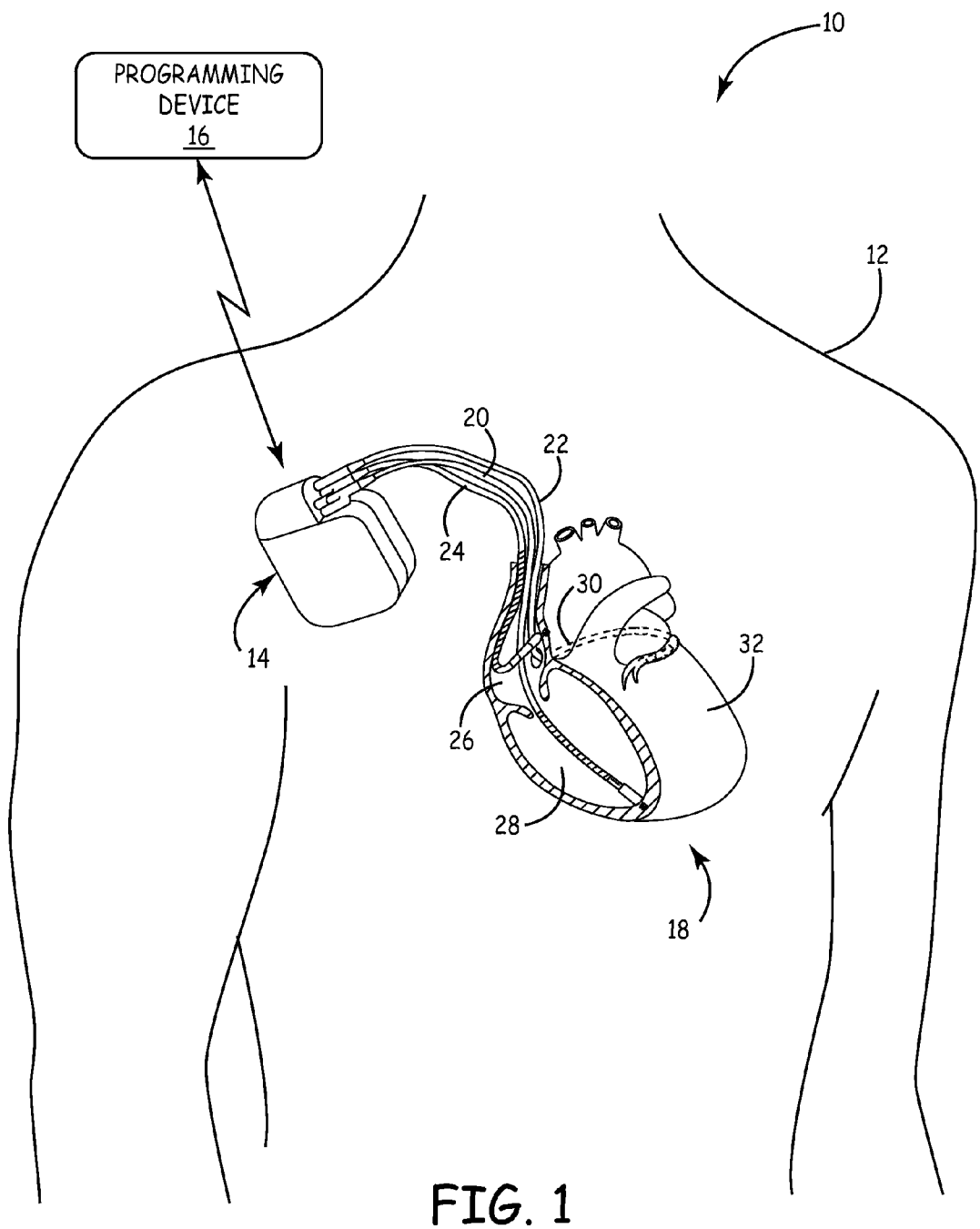
FIG. 1 is a conceptual diagram illustrating an example therapy system that may be used to provide therapy to patient.

In general, this disclosure describes techniques for detecting a condition of a patient using a probability-correlation based model that integrates a plurality of parameters associated with the condition. A medical device that operates in accordance with the techniques of this disclosure obtains a plurality of parameters associated with the condition of the patient. For each of the plurality of parameters, the medical device obtains probabilities that the condition of the patient exists based on each single parameter separately and correlations between each of the parameters and the other ones of the parameters. After obtaining the probabilities and correlations associated with each of the parameters, the medical device determines whether the condition of the patient exists based on the determined probabilities and correlations. For example, the medical device may weight each of the probabilities as a function of the correlations and sum the weighted probabilities to obtain an overall probability that the condition exists.

Such a technique may be particularly effective in discriminating between arrhythmias. For example, such a technique may be effective in discriminating between treatable arrhythmias and non-treatable arrhythmias. Treatable arrhythmias refer to abnormal rhythms for which stimulation therapy is delivered to one or both of the ventricles. Treatable arrhythmias may include ventricular tachycardia (VT) or ventricular fibrillation (VF). Non-treatable arrhythmias, on the other hand, refer to abnormal rhythms that typically do not require stimulation therapy to be delivered to either of the ventricles. Non-treatable arrhythmias may include supra-ventricular tachycardia (SVT), which includes sinus tachycardia, atrial tachycardia (AT), atrial fibrillation (AF) atrial flutter, atrio-ventricular nodal reentrant tachycardia (AVNRT), and atrio-ventricular reciprocating tachycardia (AVRT). In some instances, non-treatable arrhythmias may go untreated, i.e., no stimulation therapy is delivered to the heart. In other instances, non-treatable arrhythmias may be treated using stimulation therapy, but the stimulation therapy is not delivered to the ventricles of the patient.

Accurately determining whether the heart rhythm is treatable or non-treatable prevents inadvertent delivery of therapy to a ventricle of the patient when no therapy to the ventricle is necessary (e.g., in the case of a rhythm mischaracterized as a treatable arrhythmia) or withholding stimulation therapy when the therapy to the ventricle is necessary (e.g., in the case of a rhythm mischaracterized as a non-treatable arrhythmia). Unnecessary delivery of stimulation therapy to the patient may be uncomfortable for the patient, needlessly depletes the power source of the medical device and, in some patients or circumstances, can induce more dangerous arrhythmias.

Although this disclosure is mainly described in the context of detecting whether a heart rhythm is treatable or non-treatable, the techniques of this disclosure may be used to integrate multiple parameters together to determine whether other conditions exist based on determined probabilities of the parameters associated with the condition and correlations between each of the parameters. For example, such techniques may be used for heart failure monitoring, cardiac ischemia detection, discriminating extra-cardiac noise from true cardiac signals, epilepsy monitoring and control, non-invasive risk stratification, medical diagnostic testing, patient wellness monitoring, or in other cardiac or non-cardiac contexts.

FIG. 1 is a conceptual diagram illustrating an example therapy system 10 that may be used to provide therapy to patient 12. Therapy system 10 includes an IMD 14 and leads 20, 22 and 24 that extend from IMD 14. Therapy system 10 may also include a programming device 16 that wirelessly communicates with IMD 14.

In the example illustrated in FIG. 1, IMD 14 is an implantable cardiac device that provides electrical stimulation therapy to a heart 18 of patient 12. The electrical stimulation therapy to heart 18, sometimes referred to as cardiac rhythm management therapy, may include pacing, cardioversion, defibrillation and/or cardiac resynchronization therapy (CRT). As such, IMD 14 may operate as an implantable pacemaker, cardioverter, and/or defibrillator. The electrical stimulation therapy provided by IMD 14 depends on the arrhythmia detected by IMD 14, as described in further detail below.

IMD 14 delivers the electrical stimulation therapy to heart 18 via one or more electrodes located on leads 20, 22 and/or 24 and implanted within or adjacent to one or more atria or ventricles of heart 18. In the example illustrated in FIG. 1, leads 20, 22 and 24 are coupled to IMD 14 and extend into heart 18 of patient 12. In the example shown in FIG. 1, right ventricular (RV) lead 20 extends through one or more veins (not shown), the superior vena cava (not shown), and right atrium 26, and into right ventricle 28 of heart 18. Left ventricular (LV) coronary sinus lead 22 extends through one or more veins, the vena cava, right atrium 26, and into the coronary sinus 30 to a region adjacent to the free wall of left ventricle 32 of heart 18. Right atrial (RA) lead 24 extends through one or more veins and the vena cava, and into the right atrium 26 of heart 18. In other examples, IMD 14 may deliver stimulation therapy to heart 14 by delivering stimulation to an extravascular tissue site in addition to or instead of delivering stimulation via electrodes of intravascular leads 20, 22 and 24.

In addition to delivering therapy to heart 18, electrodes of leads 20, 22 and 24 may sense electrical signals attendant to depolarization and repolarization of heart 18 (e.g., cardiac signals). IMD 14 may analyze the sensed signals to monitor a rhythm of the heart to detect an arrhythmia of heart 18. As described above, the electrical stimulation therapy provided by IMD 14 may depend on the type of arrhythmia detected by IMD 14. For example, IMD 14 may provide stimulation therapy (e.g., ATP, defibrillation shock and/or cardioversion shock) to ventricle 28 of patient 12 in response to detecting that the rhythm is a treatable arrhythmia, e.g., VT or VF. As another example, IMD 14 may withhold delivery of stimulation therapy to ventricle 28 in response to detecting that the rhythm is a non-treatable arrhythmia, e.g., SVT. Instead, IMD 14 may deliver no therapy or provide therapy to atrium 26 to treat the SVT. As such, the non-treatable arrhythmias are non-treatable in that they do not require stimulation therapy to ventricle 28 and/or 32.

In some instances, SVT may be conducted to ventricles 28 and/or 32 and falsely detected as VT or VF. This results in IMD 14 delivering ventricular stimulation therapy (e.g., ATP, cardioversion or defibrillation) when no ventricular therapy is needed. Unnecessary delivery of electrical stimulation therapy to ventricles 28 and/or 32 may be uncomfortable for patient 12 and, in some patients, may induce dangerous arrhythmias. Additionally, delivery of unnecessary electrical stimulation therapy needlessly depletes the power source of IMD 14. It is desirable, therefore, to avoid delivering a therapy to ventricles 28 and/or 32 due to inappropriate arrhythmia detection.

The techniques of this disclosure may increase the accuracy with which IMD 14 detects arrhythmias and discriminates between treatable and non-treatable arrhythmias. In accordance with the techniques described in this disclosure, IMD 14 obtains a plurality of parameters associated with the rhythm of heart 18. IMD 14 obtains probabilities that the rhythm is treatable based on each of the plurality of parameters separately. In other words, for each of the parameters, IMD 14 determines the probability that the rhythm is treatable based on only the corresponding parameter. Additionally, IMD 14 obtains correlations between each of the parameters and the other ones of the parameters. IMD 14 then determines whether the rhythm is treatable based on the determined probabilities and correlations. For example, IMD 14 computes weights for each of the parameters based on the correlations. The weights represent the independent contribution coefficient to attribute to the respective parameters. IMD 14 computes an overall probability that the rhythm is treatable ($P_{VT/VF}$) by weighting the probabilities by the corresponding independent contribution coefficient and summing the weighted probabilities.

IMD 14 determines whether the rhythm is treatable based on the overall probability. For example, IMD 14 may compare the overall probability that the rhythm is treatable ($P_{VT/VF}$) to a threshold value and classify the rhythm as treatable if the $P_{VT/VF}$ is greater than or equal to the threshold value. Alternatively, IMD 14 may compute an overall probability that the rhythm is non-treatable ($P_{SVT}$) in the same manner as the overall probability that the rhythm is treatable, and use the overall probability that the rhythm is non-treatable ($P_{SVT}$) along with the overall probability that the rhythm is treatable ($P_{VT/VF}$) to determine whether the rhythm is treatable. For example, if $P_{VT/VF} > P_{SVT} + C$, the rhythm is classified as treatable and if $P_{SVT} > P_{VT/VF} + C$, the rhythm is classified as non-treatable, where C ensures some confidence in the decision. C may take on any value between 0 and 1. If neither of the above conditions is met, IMD 14 determines it is incapable of determining whether the rhythm is treatable or non-treatable.

A user, such as a physician, technician, or other clinician, may interact with programming device 16 to communicate with IMD 14. For example, the user may interact with programming device 16 to retrieve physiological or diagnostic information from IMD 14. For example, the user may use programming device 16 to retrieve information from IMD 14 regarding the rhythm of the heart of patient 12, trends therein over time, or cardiac arrhythmia episodes. As another example, the user may use programming device 16 to retrieve information from IMD 14 regarding other sensed physiological parameters of patient 12, such as electrical depolarization/repolarization signals from the heart (referred to as "electrogram" or EGM), intracardiac or intravascular pressure, activity, posture, respiration or thoracic impedance. As another example, the user may use programming device 16 to retrieve information from IMD 14 regarding the performance or integrity of IMD 14 or other components of therapy system 10, such as leads or a power source of IMD 14.

The user may also interact with programming device 16 to program IMD 14, e.g., select values for operational parameters of IMD 14. For electrical stimulation therapies, for example, the user may interact with programming device 16 to program one or more sets of therapy parameters, select therapy programs or progressions of therapy programs to be used during particular arrhythmias, select an electrode or combination of electrodes of leads 20, 22 and 24 to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like. By programming these parameters, the physician or other user can attempt to generate an efficacious therapy for patient 12 that is delivered via the selected electrodes.

Programming device 16 may be a dedicated hardware device with dedicated software for programming of IMD 14. Alternatively, programming device 16 may be an off-the-shelf computing device running an application that enables programming device 16 to program IMD 14. In some examples, programming device 16 may be a handheld computing device or a computer workstation. Programming device 16 may, in some instances, include a programming head that may be placed proximate to the patient's body near the implant site of IMD 14 in order to improve the quality or security of communication between IMD 14 and programming device 16. Programming device 16 may include a user interface that receives input from the user and/or displays data to the user.

Programming device 16 may communicate with IMD 14 via wireless communication using any techniques known in the art. Examples of communication techniques may include, for example, magnetic telemetry, low frequency telemetry or radiofrequency (RF) telemetry, but other techniques are also contemplated. In some instances, programming device 16 and IMD 14 may communicate in the 402-405 MHz frequency band in accordance with the Medical Implant Communications Service (MICS) protocol.

Figure 2:
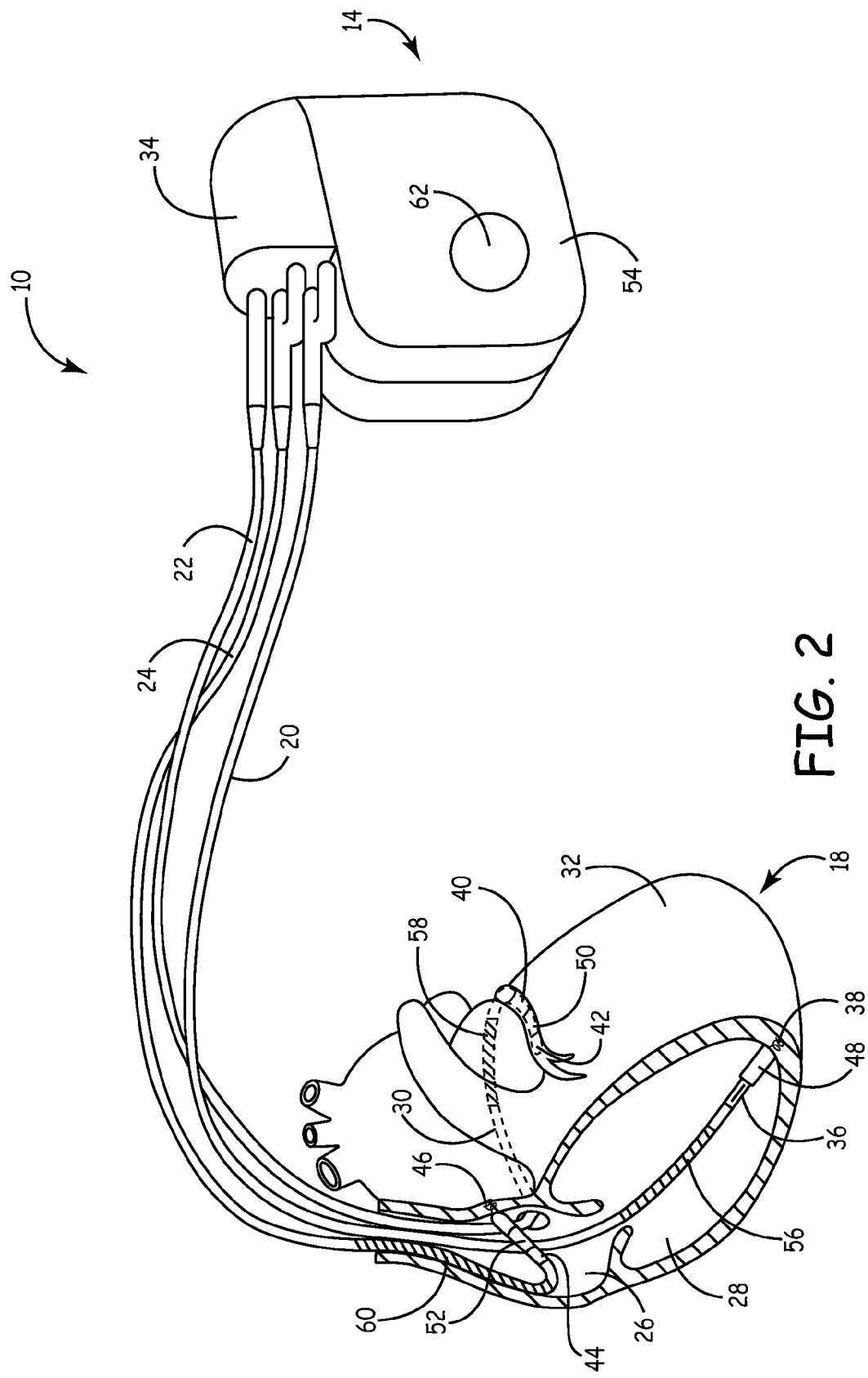
FIG. 2 is a conceptual diagram illustrating the IMD and leads of the therapy system of FIG. 1 in greater detail.

FIG. 2 is a conceptual diagram illustrating IMD 14 and leads 20, 22 and 24 of therapy system 10 in greater detail. Leads 20, 22 and 24 are electrically coupled to a stimulation module, a sensing module, or other modules of IMD 14 via connector block 34. In some examples, proximal ends of leads 20, 22 and 24 include electrical contacts that electrically couple to respective electrical contacts within connector block 34. In addition, in some examples, leads 20, 22 and 24 are mechanically coupled to connector block 34 with the aid of set screws, connection pins or another suitable mechanical coupling mechanism.

Each of the leads 20, 22 and 24 includes an elongated insulative lead body, which may carry a number of concentric coiled conductors separated from one another by tubular insulative sheaths. Other lead configurations are also contemplated, such as lead configurations that do not include coiled conductors, but instead a different type of conductor. In the illustrated example, bipolar electrodes 36 and 38 are located proximate to a distal end of lead 20. In addition, bipolar electrodes 40 and 42 are located proximate to a distal end of lead 22 and bipolar electrodes 44 and 46 are located proximate to a distal end of lead 24.

Electrodes 36, 40, and 44 may take the form of ring electrodes, and electrodes 38, 42, and 46 may take the form of extendable helix tip electrodes mounted retractably within insulative electrode heads 48, 50, and 52, respectively. Each of the electrodes 36, 38, 40, 42, 44, and 46 is electrically coupled to a respective one of the conductors within the lead body of its associated lead 20, 22 and 24, and thereby coupled to respective ones of the electrical contacts on the proximal end of leads 20, 22 and 24. In other embodiments, electrodes 36, 38, 40, 42, 44, and 46 may be other types of electrodes.

Electrodes 36, 38, 40, 42, 44, and 46 may sense electrical signals attendant to the depolarization and repolarization of heart 18. The electrical signals are conducted to IMD 14 via the one or more conductors of respective leads 20, 22 and 24. In some examples, IMD 14 also delivers pacing pulses via electrodes 36, 38, 40, 42, 44, and 46 to cause depolarization of cardiac tissue of heart 14. In some examples, as illustrated in FIG. 2, IMD 14 includes one or more housing electrodes, such as housing electrode 62, which may be formed integrally with an outer surface of hermetically-sealed housing 54 of IMD 14 or otherwise coupled to housing 54. In some examples, housing electrode 62 is defined by an uninsulated portion of an outward facing portion of housing 54 of IMD 14. In some examples, housing electrode 62 comprises substantially all of housing 54. Divisions between insulated and uninsulated portions of housing 54 may be employed to define two or more housing electrodes. Any of the electrodes 36, 38, 40, 42, 44, and 46 may be used for unipolar sensing or pacing in combination with housing electrode 62. As such, the configurations of electrodes used by IMD 14 for sensing and pacing may be unipolar or bipolar depending on the application.

Leads 20, 22 and 24 also include elongated electrodes 56, 58, and 60, respectively, which may, in some instances, take the form of a coil. IMD 14 may deliver high energy electrical shocks, e.g., defibrillation or cardioversion shocks, to heart 18 via any combination of elongated electrodes 56, 58, and 60, and housing electrode 62. In particular, IMD 14 may deliver the high energy electrical shocks in response to determining that a detected arrhythmia is treatable. Electrodes 36, 38, 40, 42, 44, 46, 56, 58, 60, and 62 may be fabricated from any suitable electrically conductive material, including, but not limited to, platinum, platinum alloy or other materials known to be usable in implantable defibrillation electrodes.

The configuration of therapy system 10 illustrated in FIGS. 1 and 2 are merely examples. In other examples, therapy system 10 may include more or fewer leads extending from IMD 14. For example, IMD 14 may be coupled to two leads, e.g., one lead implanted within right atrium 26 and the other implanted within right ventricle 28. In another example, IMD 14 may be coupled to a single lead that is implanted within either an atrium or ventricle of heart 18. As a further example, the therapy system may include three transvenous leads located as illustrated in FIGS. 1 and 2, and an additional lead located within or proximate to left atrium 32. As such, IMD 14 may be used for single chamber or multi-chamber cardiac rhythm management therapy. In addition to more or fewer leads, each of leads 20, 22 and 24 may include more or fewer electrodes.

In still other examples, a therapy system may include epicardial leads and/or patch electrodes instead of or in addition to the transvenous leads 20, 22 and 24 illustrated in FIGS. 1 and 2. In other words, IMD 14 may be a subcutaneous cardiac device. Further, IMD 14 need not be implanted within patient 12. In examples in which IMD 14 is not implanted in patient 12, IMD 14 may deliver defibrillation pulses and other therapies to heart 18 via percutaneous leads that extend through the skin of patient 12 to a variety of positions within or outside of heart 18.

The techniques of this disclosure are described in the context of characterizing heart rhythms for cardiac rhythm management therapy for purposes of illustration. The techniques of this disclosure, however, may be used in other contexts. For example, IMD 14 may obtain a plurality of parameters associated with heart failure, such as patient activity (e.g., from an accelerometer inside housing 54), heart muscle activity (contractility of myocardium measured from an accelerometer on one of lead 20, 22 or 24), heart sounds, blood pressure, impedance, tissue color, or heart rate variability. IMD 14 obtains the probability that heart failure exists based on each of the parameters individually, obtains correlations between each of the parameters and the other ones of the parameters, and determines whether heart failure exists based on the determined probabilities and correlations.

As another example, IMD 14 may obtain a plurality of parameters associated with ischemia, such as beat morphology parameters from multiple different EGM sensing vectors and the parameters extracted from heart sounds. IMD 14 obtains the probability that ischemia exists based on each of the parameters individually, obtains correlations between each of the parameters and the other ones of the parameters, and determines whether cardiac ischemia exists based on the determined probabilities and correlations.

In another example, IMD 14 may obtain a plurality of parameters associated with an electrical signal and use the probability-correlation based model to more accurately discriminates between extra-cardiac noise (e.g. electromagnetic interference, electrocautery or the like) and cardiac noise sources (T-wave oversensing, R-wave double counting, far-field R-wave oversensing) from true cardiac signals.

In a further example, IMD 14 may obtain a plurality of parameters associated with non-invasive risk stratification, such as heart rate variability, baroreflex sensitivity, T-wave alternates, heart rate turbulence, QRS duration, and QT dispersion. IMD 14 may combine these parameters together using the probability-correlation based model described herein into a more accurate risk stratification decision.

The techniques of this disclosure may also be used outside of cardiac contexts. For example, an IMD may obtain parameters associated with epilepsy monitoring and control, such as a complexity measure, silent period, entropy, time and frequency domain features extracted from EEG (brain-wave) signals. The IMD obtains probabilities that epilepsy exists based on each of the parameters individually, obtains correlations between each of the parameters and the other ones of the parameters, and determines whether epilepsy exists based on the determined probabilities and correlations. In this manner, the techniques may provide for a closed-loop monitoring and stimulation control for epilepsy.

In another example, the IMD may obtain a plurality of parameters associated with wellness, such as heart rate variability, heart rate acceleration and deceleration, patient activity, acoustic cardiographic parameters (such as time intervals between QRS (Q, R, and S-waves) and heart sounds (S1 and S2 sounds), e.g., Q-S1 interval, S1-S2 interval, S2-P interval, P-S1 interval, or the ratios of these intervals to R-R interval, blood pressure, weights, medicine uses, or the like. The IMD may combine these parameters together using the probability-correlation based model described herein to generate a health index. The health index can be computed and/or used by the IMD or a monitoring module inside a standalone device or an integrated monitoring station.

In a further example, IMD 14 may obtain a plurality of parameters associated with a diagnosis test for a disease or condition, such as parameters associated with making a diagnosis for cancer or HIV. IMD 14 may combine these parameters together using the probability-correlation based model described herein to generate a more accurate diagnosis of the particular disease or condition. As such, description of these techniques in the context of cardiac rhythm management therapy should not be considered limiting of the techniques as broadly described in this disclosure.

Figure 3:
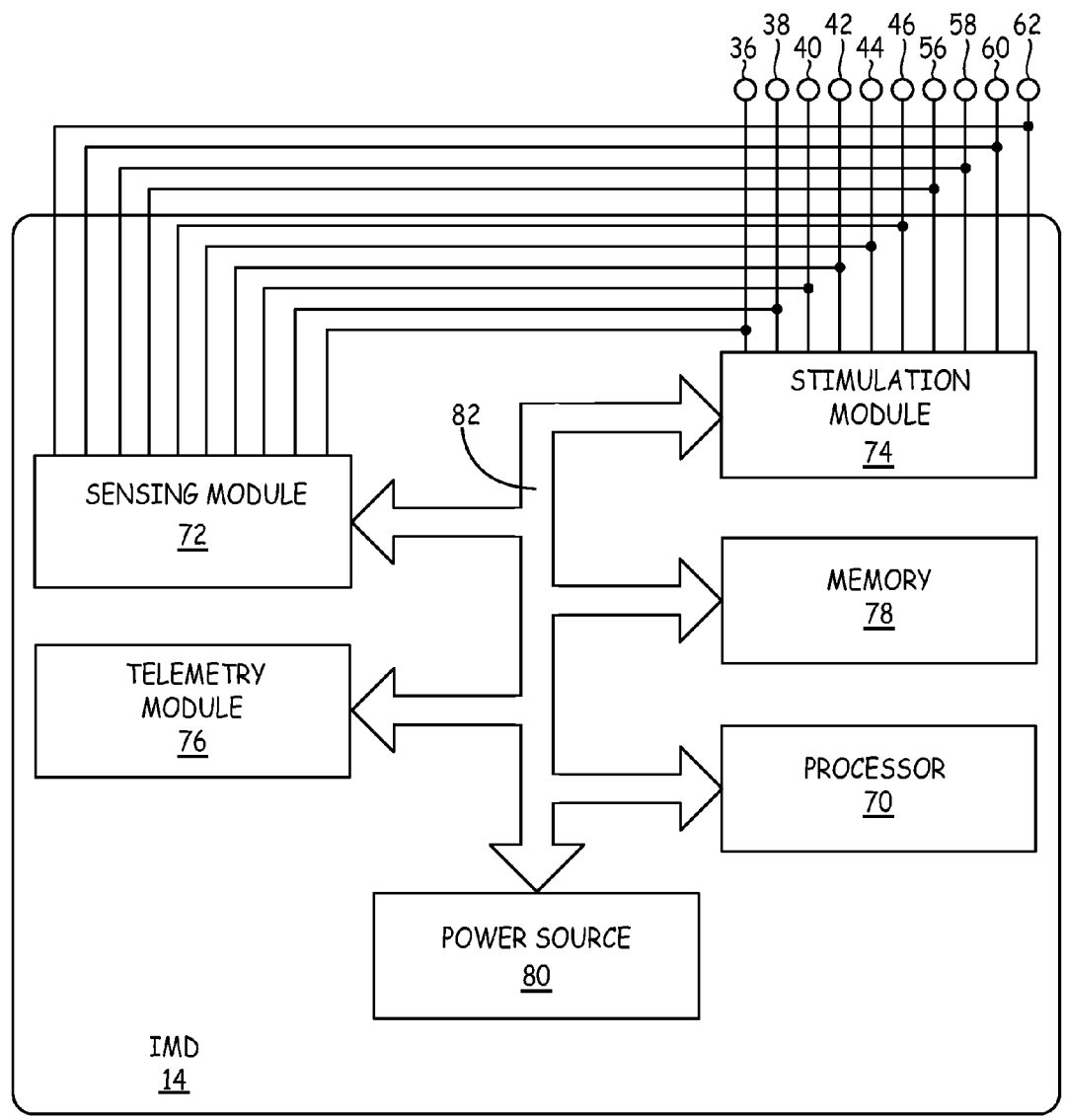
FIG. 3 is a functional block diagram of an example configuration of components of an IMD.

FIG. 3 is a functional block diagram of an example configuration of components of IMD 14. In the example illustrated by FIG. 3, IMD 14 includes a processor 70, sensing module 72, stimulation module 74, telemetry module 76, memory 78, and power source 80. The various components of IMD 14 are interconnected by a data bus 82. In other examples, the various components of IMD 14 may be interconnected by a number of point-to-point connections or a combination of one or more data buses and one or more point-to-point connections.

Processor 70 may include one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Memory 78 may include computer-readable instructions that, when executed by processor 70, cause components of IMD 14 to perform various functions attributed to the respective components in this disclosure. Memory 78 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The various components of IMD 14 are coupled to power source 80, which may include a non-rechargeable battery, rechargeable storage device such as a rechargeable battery or capacitor (which may be recharged internally or transcutaneously with the use of electromagnetic or piezoelectric transformers), energy-harvesting device, or a combination thereof. A non-rechargeable battery may be capable of holding a charge for several years, while a rechargeable battery may be inductively charged from an external device, e.g., on a daily or weekly basis. Power source 80 also may include power supply circuitry (not shown in FIG. 3) for providing regulated voltage and/or current levels to power the components of IMD 14.

Processor 70 controls electrical stimulation module 74 to deliver stimulation therapy to heart 18. Processor 70 may control electrical stimulation module 74 to deliver stimulation according to a selected one or more therapy programs, which may be stored in memory 82. For example, processor 70 may control electrical stimulation module 74 to deliver electrical pacing pulses, cardiac resynchronization pulses, or cardioversion or defibrillation shocks with the amplitudes, pulse widths, frequencies, and/or electrode polarities specified by the selected therapy programs. The type of therapy program provided may, for example, be dependent on the type of arrhythmia detected, whether a previous therapy program was effective, or the like.

Electrical stimulation module 74 is electrically coupled to electrodes 36, 38, 40, 42, 44, 46, 56, 58, 60, and 62, e.g., via conductors of the respective lead 20, 22 and 24, or, in the case of housing electrode 62, via an electrical conductor disposed within housing 54 of IMD 14. Electrical stimulation module 74 may include a switch module (not shown in FIG. 3) and processor 70 may use the switch module to select, e.g., via a data/address bus 82, which of the available electrodes to us to deliver pacing, resynchronization, cardioversion, or defibrillation pulses/shocks. The switch module may include a switch array, switch matrix, multiplexer, or any other type of switching device suitable to selectively couple stimulation energy to selected electrodes.

Sensing module 72 is configured to receive signals sensed by one or more sensors connected to sensing module 72. Sensing module 72 is electrically coupled to electrodes 36, 38, 40, 42, 44, 46, 56, 58, 60, and 62, e.g., via conductors of the respective lead 20, 22 and 24, or, in the case of housing electrode 62, via an electrical conductor disposed within housing 54 of IMD 14. In this case, electrodes 36, 38, 40, 42, 44, 46, 56, 58, 60, and 62 are the sensors connected to sensing module 72. Sensing module 72 may include a switch module and processor 80 may use the switch module to select, e.g., via a data/address bus 82, which of the available electrodes are used to sense electrical cardiac signals of heart 18. In this manner, sensing module 72 is capable of monitoring signals from a variety of electrode sensing vectors formed by different combinations of electrodes 36, 38, 40, 42, 44, 46, 56, 58, 60, and 62. The switch module may include a switch array, switch matrix, multiplexer, or any other type of switching device suitable to selectively couple the selected electrodes to the sensing circuitry of sensing module 72. In some instances, sensing module 72 and therapy module 74 may share a switch module.

Sensing module 72 may receive signals sensed by various other sensors instead of, or in addition to, the signals sensed by the combinations of electrodes 36, 38, 40, 42, 44, 46, 56, 58, 60 and 62. For example, sensing module 72 may receive signals from one or more sensors that sense intravascular pressure, blood pressure, blood flow, acceleration, displacement, motion, respiration, or blood/tissue chemistry such as oxygen saturation, carbon dioxide, pH, protein levels, enzyme levels or other physiological parameter. Sensing module 72 may couple to these various other sensors via a wired connection or a wireless connection, e.g., using telemetry module 76.

Sensing module 72 may store the sensed signals in memory 78. In some instances, sensing module 72 may store the sensed signals in raw form. In other instances, sensing module 72 may process the sensed signals and store the processed signals in memory 78. For example, sensing module 72 may amplify and filter the sensed signal and store the filtered signal in memory 78. The signals stored by sensing module 72 may, in some cases, be retrieved and further processed by processor 70. Additionally, processor 70 may control telemetry module 76 to send the signals stored by sensing module 72 to another device, such as IMD 14, programming device 16 or monitoring device 19 of FIG. 1.

Under the control of processor 70, telemetry module 76 may receive data from and send data to programming device 16 with the aid of an antenna, which may be internal and/or external to IMD 14. Telemetry module 76 includes any suitable hardware, firmware, software or any combination thereof for communicating with another device. For example, telemetry module 76 may include appropriate modulation, demodulation, frequency conversion, filtering, and amplifier components for transmission and reception of data.

As described above, the type of therapy program provided by stimulation module 74 may be dependent on the type of heart rhythm detected, e.g., whether it is treatable (e.g., VT/VF) or non-treatable (e.g., SVT). Processor 70 controls stimulation module 74 to deliver electrical stimulation therapy to at least one ventricle of patient 12 in response to detecting the rhythm is treatable. For example, processor 70 may control stimulation module 74 to deliver a cardioversion shock in response to detecting VT or control stimulation module 74 to deliver a defibrillation shock in response to detecting VF. As another example, processor 70 may control stimulation module 74 to deliver ATP to at least one ventricle of patient 12 in response to detecting the rhythm as treatable. In other examples, processor 70 may control stimulation module 74 to deliver a progression of therapies, e.g., shocks with increasing energy levels or various anti-tachycardia pacing regimens followed by shocks in response to detecting the rhythm as treatable.

Rhythms detected to be non-treatable, on the other hand, do not require stimulation therapy to be delivered to the ventricles of patient 12. In fact, non-treatable rhythms may not be treated at all. In instances in which non-treatable rhythms are treated, however, stimulation module 74 does not deliver therapy to the ventricles of patient 12. Instead, stimulation module 74 may deliver therapy to other locations, including one or both atria.

Sometimes, a non-treatable arrhythmia (e.g., SVT) is conducted to the ventricles and falsely detected as VT or VF, resulting in the delivery of ventricular cardioversion, defibrillation or ATP therapy when no ventricular therapy is needed. Unnecessary delivery of ventricular therapy is generally uncomfortable for patient 12, needlessly depletes power source 80 and can sometimes induce more dangerous arrhythmias (e.g., actual VT or VF). It is desirable, therefore, to avoid delivering a ventricular stimulation therapy due to inappropriate detection of ventricular arrhythmias.

In accordance with the rhythm classification techniques of this disclosure, multiple parameters associated with the rhythm of heart 18 are analyzed using a probability-correlation based model to determine whether the rhythm is treatable or non-treatable. These techniques increase the reliability of discrimination between treatable and non-treatable arrhythmias and reduce the likelihood of delivery of unnecessary electrical stimulation to heart 18 and particularly to the ventricles of heart 18.

In particular, processor 70 analyzes the sensed signals obtained by sensing module 72 to obtain parameters that characterize the rhythm of heart 18 of patient 12. Processor 70 may analyze the rhythm over a period of time to generate a plurality of morphology parameters, e.g., x1, x2 and x3 for purposes of description. In one example, processor 70 analyzes the rhythm over a period of time that encompasses a single ventricular event, e.g., a 200 ms time window surrounding a sensed ventricular event. As such, processor 70 may be viewed as analyzing the rhythm on a beat-by-beat basis. In another example, processor 70 may analyze the rhythm over a longer period of time that includes more than one ventricular event, e.g., over a 3-second window. Processor 70 may analyze the rhythm over windows of any length of time. More or fewer than three parameters may be obtained by processor 70 via the analysis of the rhythm as described in more detail below.

For example, processor 70 may compare a far-field and near-field EGM signals to respect template signals to obtain a far-field and near-field wavelet matching score (WMS). Additionally, or alternatively, processor 70 may analyze the far-field and near-field EGM signals during the portion or window of the EGM to obtain a number of beat morphology parameters. Far-field beat morphology parameters may include an R-wave symmetry index (RSI) that represents the ratio of onset-side slope to offset-side slope of the R-wave in the far-field EGM, R-wave width (RW) value that represents the width of the R-wave in the far-field EGM, Q-wave R-wave index (QRI) that represents the ratio of the Q-wave amplitude to the R-wave amplitude in the far-field EGM, R-wave polarity code (RPC) value that represents the R-wave polarities between the far-field EGM and the near-field EGM, and slope peak shift (SPS) that represents the time difference in slope peaks between the far-field EGM and the near-field EGM. Calculation of these beat morphology parameters will be described in more detail below.

Other types of morphology parameters may also be used in addition to or instead of the beat morphology parameters described above. For example, processor 70 may analyze the rhythm over the period of time (e.g., 3-second window) to compute any of a number of gross morphology parameters. The gross morphology parameters characterize the morphology of the ECG over the period of time and may include more than one beat. Beat morphology parameters, on the other hand, are morphology parameters of a single beat.

Gross morphology parameters may include a low slope content (LSC), normalized mean rectified amplitude (NMRA) spectral width (SW), or signal overall variability. LSC may be the ratio of the number of data points with low slope to the total number of samples in the 3-second segment. SW is an approximation of the signal bandwidth. SW may be defined as the fundamental period (i.e., the inverse of the fundamental frequency or heart rate (HR)) minus the mean period (the inverse of the mean frequency). Mean frequency (MF) is calculated as the ratio of the mean absolute amplitude of the first derivative of the 3-second segment to the mean absolute amplitude of the 3-second segment, and the ratio is roughly proportional to the frequency of the dominant sinusoidal component in the 3-second segment. NMRA characterizes how wide the overall signal pulse waveform is, and is estimated as the ratio of the averaged rectified amplitude of the 3-sec segment to the maximum rectified amplitude value of the 3-sec segment. SOV is calculated as the ratio of sum of the absolute difference between a 3-sec segment waveform and the corresponding shifted (by half of the mean of the first 6 RR intervals in a sorted (from small to large) latest 12 RR interval buffer) 3-sec segment waveform to the sum of the absolute value of the 3-sec segment.

Moreover, other non-morphology parameters may also be used such as heart rate, intracardiac or intravascular pressure, oxygen saturation, blood pressure, blood flow, tissue perfusion, impedance, heart sounds, motion or the like. In other words, IMD 14 may integrate information from hemodynamic sensors with EGM information or use the information from the hemodynamic sensors instead of the EGM information in determining whether a rhythm is treatable or non-treatable.

Each of the parameters obtained by processor 70 has a different discrimination capability or probability to predict the condition. In other words, each of the parameters on its own may be indicative of whether the condition exists, e.g., whether a rhythm is treatable or non-treatable in this example. However, none of the parameters on their own provide a perfect indication of whether the rhythm is treatable or non-treatable. Therefore, it is desirable to combine more than two of the parameters in making the determination as to whether the condition exists. The techniques of this disclosure combine two or more of the morphological parameters based on the probabilities that each parameter is indicative of the condition (e.g., the discrimination power) and the correlation between each of the parameters and the other parameters.

After processor 70 obtains the parameters associated with the rhythm, processor 70 determines a probability (or discrimination power) that the condition exists for each of the parameters individually. For example, processor 70 may obtain a probability for each of the parameters that represents the probability that the rhythm is classified as treatable based solely on the value of the particular morphological parameter. Continuing the example from above, processor 70 may compute probability p1 that represents the probability the rhythm is treatable based solely on the value of parameter x1, probability p2 that represents the probability the rhythm is treatable based solely on the value of parameter x2, and probability p3 that represents the probability the rhythm is treatable based solely on the value of parameter x3. Processor 70 may obtain the probability associated with each of the parameters using a look-up table stored in memory 78 or an equation that estimates a probability curve associated with the particular parameter. The look-up table or equation stored in memory 78 may be generated based on a candidate data set that includes data from a number of VF, VT and SVT episodes and/or beats experienced by one or more patients.

Processor 70 also obtains an independent contribution coefficient associated with each of parameters. The independent contribution coefficient represents the independent contribution of the particular morphological parameter to the overall probability that the condition exists. The independent contribution coefficient is computed based on the correlation coefficients among the various parameters. If processor 70 analyzes the three morphological parameters in the example above, i.e., x1, x2 and x3, the independent contribution coefficient for each of the morphological parameters are w1=(2−c12−c13), w2=(2−c12−c23) and w3=(2−c13−c23), respectively, where c12 is the correlation between x1 and x2, c23 is the correlation between x2 and x3 and c13 is the correlation between x1 and x3. Processor 70 may use the independent contribution coefficients to weight the probabilities of each of the morphological parameters (e.g., p1, p2 and p3 in our example). Processor 70 may obtain the independent contribution coefficients and/or the correlations between each of the parameters from a look-up table stored within memory 78.

Processor 70 uses the obtained probabilities and independent contribution coefficients to compute an overall probability P that the condition exists in accordance with the equation below:

$$P = \sum_{i=0}^{n} w_i * p_i, \quad (1)$$

where $w_i$ is the independent contribution coefficient of the $i^{th}$ parameter, $p_i$ is the discrimination power (probability) of the $i^{th}$ parameter and n is equal to the number of parameters. In particular, processor 70 multiplies each of the probabilities associated with the individual parameters by the corresponding independent contribution coefficient to obtain weighted probabilities for each morphological parameter and sums the weighted probabilities to obtain the overall probability P.

Processor 70 determines whether or not the condition exists based on the overall probability P that the condition exists. Processor 70 may compare the overall probability P that the condition exists to a threshold value and determine that the condition exists when P is greater than or equal to the threshold value. For example, processor 70 may compare the overall probability that the rhythm is treatable ($P_{VT/VF}$) to a threshold value and classify the rhythm as treatable if the $P_{VT/VF}$ is greater than or equal to the threshold value.

Alternatively, processor 70 may compute an overall probability that the rhythm is non-treatable ($P_{SVT}$) in the manner described above and use the overall probability that the rhythm is non-treatable $P_{SVT}$ along with the overall probability that the rhythm is treatable $P_{VT/VF}$ to classify the rhythm. For example, if $P_{VT/VF} > P_{SVT} + C$, processor 70 classifies the rhythm classified as treatable. If $P_{VT/VF} < P_{SVT} + C$, processor 70 determines if $P_{SVT} > P_{VT/VF} + C$. If so, processor 70 classifies the rhythm as non-treatable. If neither of the above conditions is met, processor 70 determines it is incapable of determining whether the rhythm is treatable or non-treatable. In this manner C serves as a measure of confidence in the decision. In some instances C may be equal to zero.

Processor 70 controls stimulation module 74 to deliver a high energy shock (e.g., cardioversion or defibrillation shock) to heart 18 based upon the classification of the rhythm. If the rhythm is determined to be non-treatable, stimulation module 74 does not deliver electrical stimulation to the ventricles. Instead, stimulation module 74 may deliver therapy to one or both atria or provide no therapy at all. If the rhythm is determined to be treatable, however, stimulation module 74 delivers ventricular stimulation therapy, e.g., in the form of ATP, cardioversion shock(s), defibrillation shock(s) or a combination thereof. Processor 70 may further analyze the rhythm to further differentiate the type of treatable arrhythmia. For example, processor 70 may analyze the rate and regularity of the rhythm to determine whether the treatable rhythm is VT or VF. In the case of VT, stimulation module 74 may provide ATP and/or cardioversion may be delivered. In the case of VF, stimulation module 74 may deliver a defibrillation shock.

Figure 4:
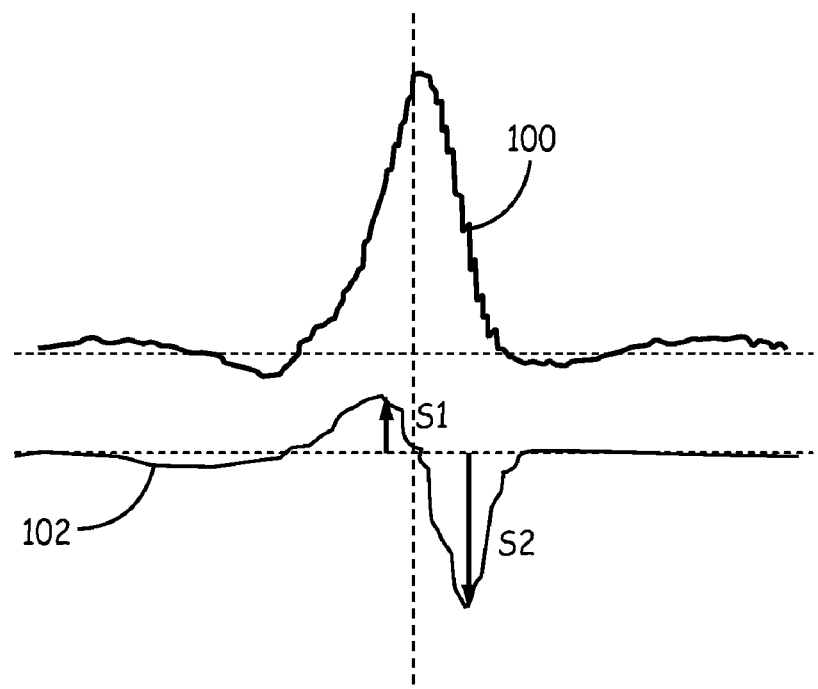
FIGS. 4-8 are timing diagrams illustrating example EGMs over a period of time and techniques for computing various beat morphology parameters using the EGMs.

FIGS. 4-8 are timing diagrams illustrating example portions of EGMs over a period of time and techniques for computing various beat morphology parameters using the EGMs. FIG. 4 is timing diagram illustrating an example portion of a far-field EGM signal 100 of a heart beat and a technique to compute the RSI of far-field EGM signal 100. Below the far-field EGM signal 100 is a curve 102 that represents the slope of far-field EGM signal 100. Processor 70 of IMD 14 computes a peak value of the onset-side slope (labeled S1 in FIG. 4) and a peak value of the offset-side slope (labeled S2 in FIG. 4). The RSI is computed as the absolute value of the ratio of the onset-side slope to offset-side slope of the far-field EGM multiplied by the factor of 10. Multiplying by the factor of 10 converts the RSI value to resolution 10. In other examples, other resolutions may be used.

Figure 5:
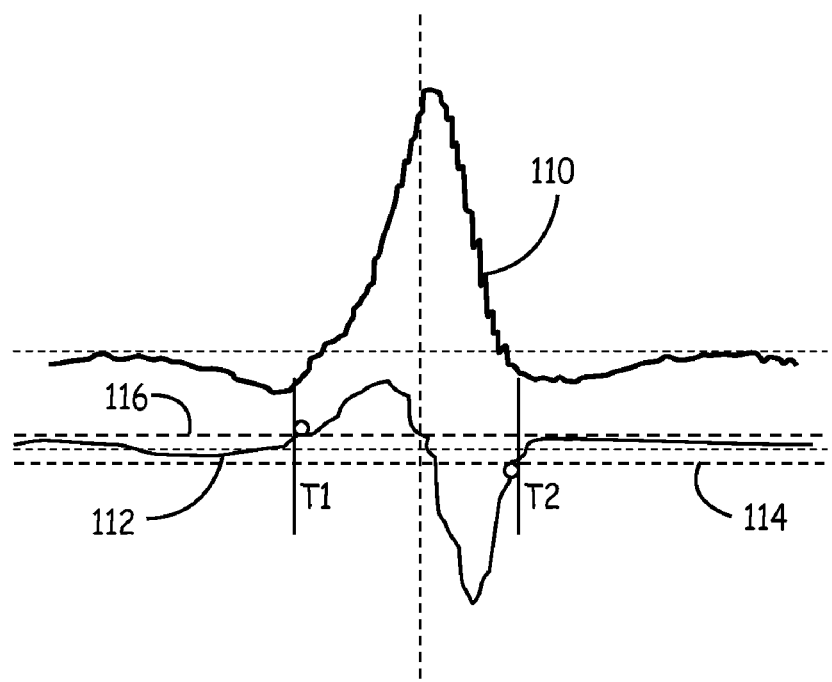

FIG. 5 is a timing diagram illustrating another example portion of a far-field EGM signal 110 and a technique for computing the RW of far-field EGM signal 110. Below the far-field EGM signal 110 is a curve 112 that represents the slope of far-field EGM signal 110. Processor 70 of IMD 14 computes overall maximum absolute peak value, referred to herein as Max_Slope, from the portion of the EGM. RW is equal to the time (labeled T2 in FIG. 5) at which the offset slope is equal to ⅛ of the Max_Slope (represented by dashed line 114) minus the time (labeled T1 in FIG. 5) at which the onset slope is equal to ⅛ of the Max_Slope (represented by dashed line 116).

Figure 6:
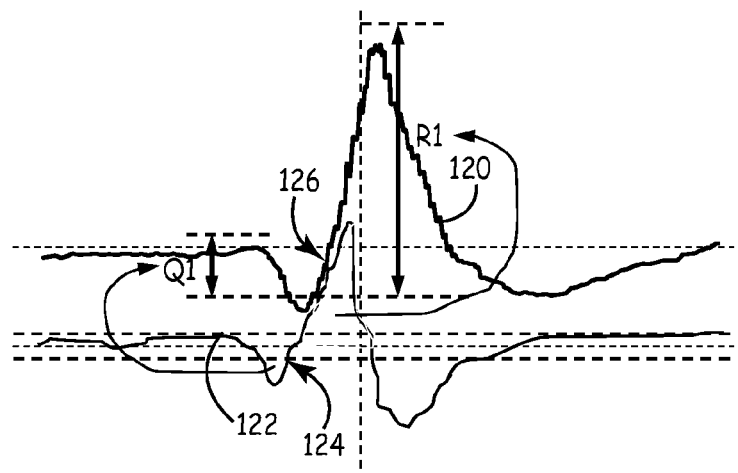

FIG. 6 is a timing diagram illustrating another example portion of a far-field EGM signal 120 and a technique for computing the QRI of far-field EGM signal 120. Below the far-field EGM signal 120 is a curve 122 that represents the slope of far-field EGM signal 120. Processor 70 of IMD 14 computes a peak amplitude of a Q-wave of far-field EGM signal 120 (labeled Q1 in FIG. 6) and a peak amplitude of an R-wave of far-field EGM signal 120 (labeled R1 in FIG. 6). The QRI is computed as the absolute value of the ratio of the peak amplitude of a Q-wave to the peak amplitude of a R-wave of the far-field EGM multiplied by the factor of 10. This ratio may be obtained by computing the ratio of the integration of the amplitude of the left side lobe pulse 124 of the slope signal to the integration of the amplitude of the main pulse 126 of the slope signal multiplied by 10. Multiplying by the factor of 10 converts the QRI value to resolution 10. In other examples, other resolutions may be used.

Figure 7:
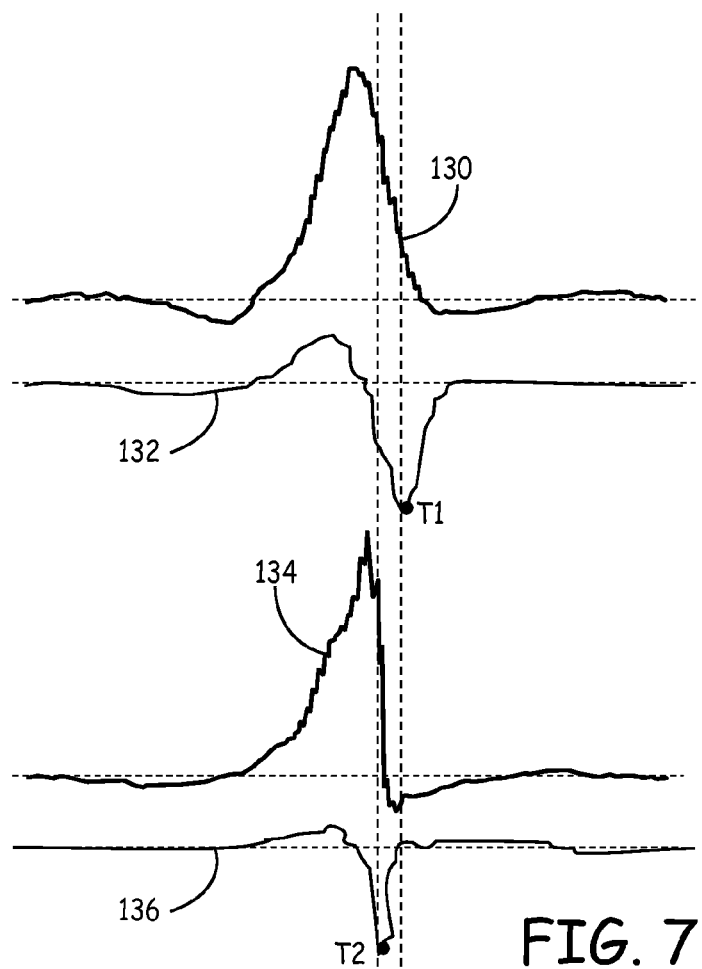

FIG. 7 is a timing diagram illustrating an example portion of a far-field EGM signal 130 and a near-field EGM signal 134. Below each of the EGM signals 130 and 134 are curves 132 and 136 that represent the slopes of far-field EGM signal 130 and near-field EGM signal 134, respectively. Processor 70 of IMD 14 computes a time at which the slope of far-field EGM signal 130 has a peak amplitude (labeled T1 in FIG. 7) and a time at which the slope of near-field EGM signal 134 has a peak amplitude (labeled T2 in FIG. 7). Processor 70 computes SPS as the difference between T1 and T2 (i.e., T1−T2).

Figure 8:
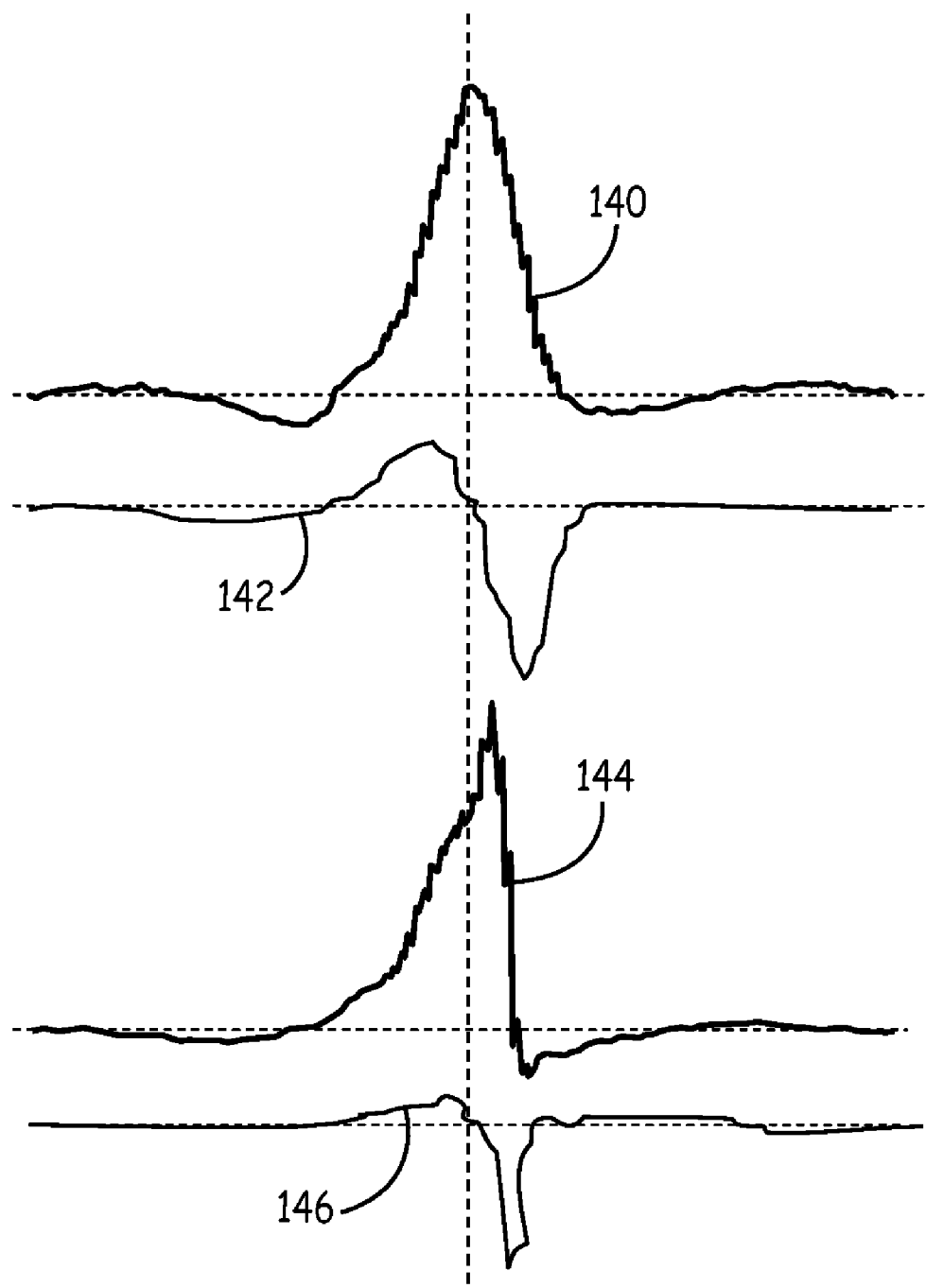

FIG. 8 is a timing diagram illustrating example portion of a far-field EGM signal 140 and a near-field EGM signal 144. Below each of the EGM signals 140 and 144 are curves 142 and 146, respectively, that represent the slopes of far-field EGM signal 140 and near-field EGM signal 144. Processor 70 of IMD 14 determines a polarity (i.e., + or −) of far-field EGM signal 140 and a polarity (i.e., + or −) of near-field EGM signal 144. Processor 70 may determine the polarity of the R-wave of the near-field and far-field EGMs using the main pulse and either the left side lobe pulse or right side lobe pulse. In particular, processor 70 may identify a positive polarity of the EGM signal when a peak-valley pattern is identified in the slope signal and identify a negative R-wave polarity of the EGM signal when a valley-peak pattern is identified in the slope signal. The RPC is the combination of polarity of the far-field EGM signal and the polarity of the near-field EGM, and takes on one of four values; ++, +−, −+ or −−. Among beats with changed RPC relative to the template, approximately 89% are VT/VF beats and among beats without changed RPC relative to the template, approximately 36% are VT/VF beats.

Processor 70 of IMD 14 may calculate the beat morphology parameters as described in detail below. Other techniques for calculating the beat morphology parameters may be used, however. As such, the description below is only one example way in which the morphology parameters may be computed. Initially, processor 70 obtains a portion of a far-field EGM around a beat of interest. The portion of the EGM may, for example, include forty-eight data points centered at a ventricular sense marker of the beat of interest. Processor 70 initially obtains a slope (first order derivative) of the input data in the window, and if the max slope (MaxSlope)≧96 ADC units (i.e., 24 mV per second) processor 70 continues to calculate beat morphology parameters. If MaxSlope<96, feature LowSlope is detected and no further calculation is performed.

Processor 70 searches for any possible positive or negative pulse in the slope signal, no matter how big or small, wide or narrow the pulse is. For each pulse in the slope signal, processor 70 calculates the characteristics of the pulse, including polarity, peak position (i.e., the data point in the window with max absolute amplitude), peak value (i.e., max absolute value in ADC counts), width (in data points), start point, end point, and "mergeable flag." If a pulse has a width<3 data points and peak value<224 ADC counts (218.75 uV), then the mergeable flag is set.

Processor 70 identifies all of the pulses in the slope signal with peak values larger than one-eighth of the MaxSlope and that are not mergeable (as indicated by the mergeable flag) and labels these pulses as large_pulses. Processor 70 then starts merging the instantly neighboring large_pulses, which are side by side to each other with the same polarity and not separated by any other large_pulse with opposite polarity. After the merging, the characteristics of the merged pulse are updated accordingly.

Processor 70 then searches for the main pulse of the slope signal, which is the merged pulse with the largest peak value. Processor 70 may also search for any possible nearest left side lobe pulse and right side lobe pulse with opposite polarity to the main pulse. Processor 70 determines the polarity of the R-wave using the main pulse and either the left side lobe pulse or right side lobe pulse. In particular, processor 70 may identify a positive R-wave polarity of the EGM signal when a peak-valley pattern is identified in the slope signal and identify a negative R-wave polarity of the EGM signal when a valley-peak pattern is identified in the slope signal.

Processor 70 calculates the QRI (in resolution 10) as the ratio of the integration of the amplitude of the left side lobe pulse of the slope signal to the integration of the amplitude of the main pulse of the slope signal multiplied by 10. Processor 70 computes the RSI (in resolution 10) as the ratio of the peak values of the two paired pulses multiplied by ten. Processor 70 also calculates the RW (in data points), SPS (in data points) from the corresponding FF and NF beats, and also RPC ("1" means both far-field and near-field R-waves have positive polarity, "2" means far-field R-wave has positive polarity and near-field R-wave has negative polarity, "3" means far-field R-wave has negative polarity and near-field R-wave has positive polarity, and "4" means both far-field and near-field R-waves have negative polarity).

Processor 70 may perform a similar analysis of a portion of a template EGM to obtain beat morphology parameters for a template beat to which the beat morphology parameters of the beat of interest are compared. The beat morphology parameters of the template beat may be stored within memory 78 for later retrieval and comparison by processor 70. As described above, the techniques for computing the beat morphology parameters described above are just one technique for determining the values of the beat morphology parameters. Other techniques may be used to compute these various beat morphology parameters.

Figure 17:
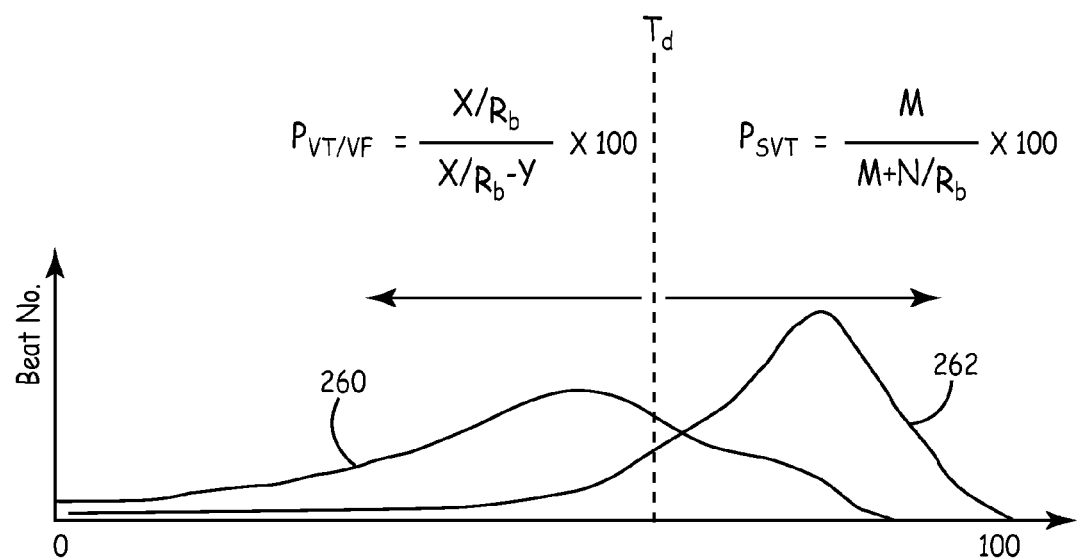
FIG. 17 is a graph illustrating a probability curve for a beat morphology parameter.

FIGS. 9-14 are graphs of probability curves for a number of morphology parameters. The probability curves plotted in the graphs of FIGS. 9-14 were generated using a probability distribution function created from a database of SVT and VT/VF beats. The database included 19,154 SVT beats and 22,765 VT/VF beats based on episode truth. The overall VT/VF to SVT beat ratio ($R_b$) of the database is 1.1885. First, the probability of VT/VF beats is calculated. For a particular parameter threshold ($T_d$), there are X number of VT/VF beats of the database that cross $T_d$. With reference to the parameter illustrated in FIG. 17, for instance, which may be a beat-morphology parameters such as near-field and far-field WMS, "cross" means less than or equal to $T_d$ for calculating the probability of the VT/VF beats. However, for calculating the probability of the VT/VF beats for other parameters like RW, RSI, QRI, SPS, and RPC, "cross" may mean greater than or equal to $T_d$. Y is the number of SVT beats of the database among all of the beats of the database that cross $T_d$. Again, for the parameter illustrated in FIG. 17 "cross" may mean less than or equal to $T_d$ for calculating the probability of the SVT beats. By using $T_d$ as a threshold for VT/VF beat detection, the VT/VF beat probability ($P_{VT/VF}$) curve 260 is estimated as:

$$P_{VT/VF} = \frac{X/R_b}{X/R_b + Y} \times 100 \quad (2)$$

$P_{VT/VF}$ may be viewed as being the discrimination power (probability) of VT/VF beats corresponding to the detection threshold $T_d$. By varying $T_d$, the probability curve for VT/VF beats can be obtained. The number of VT/VF beats X is normalized by the VT/VF to SVT ratio $R_b$ so that total number of VT/VF beats is equal to the total number of SVT beats.

The probability of SVT beats is calculated using the same threshold $T_d$. However, "cross," in the context of the parameter of FIG. 17 means greater than or equal to $T_d$ instead of less than or equal to $T_d$ as used above to compute the probability of VT/VF beats. There are M number of SVT beats of the database that cross $T_d$ (i.e., "cross" meaning "greater than or equal to") and N number of VT/VF beats of the database among all of the beats of the database that cross $T_d$ (again, "cross" meaning "greater than or equal to"). For other parameters such as RW, RSI, QRI, SPS, and RPC, cross may mean less than or equal to $T_d$. As such, the SVT beat probability ($P_{SVT}$) curve 262 may be estimated in a similar manner as:

$$P_{SVT} = \frac{M}{M + N/R_b} \times 100 \quad (3)$$

$P_{SVT}$ may be viewed as being the discrimination power (probability) of SVT beats corresponding to the detection threshold $T_d$. By varying $T_d$, the probability curve for SVT beats can be obtained in much the same manners as $P_{VT/VF}$. Again, the number of VT/VF beats N is normalized by the VT/VF to SVT ratio $R_b$ so that total number of VT/VF beats is equal to the total number of SVT beats.

As can be seen, the $P_{VT/VF}$ and $P_{SVT}$ calculations are based on the assumption that the device will see equal number of SVT-beat and VT/VF-beat. However, the ratio of SVT-beat to VT-beat can be estimated from clinical studies and it might also change with populations, e.g., primary vs. secondary prevention.

Figure 9:
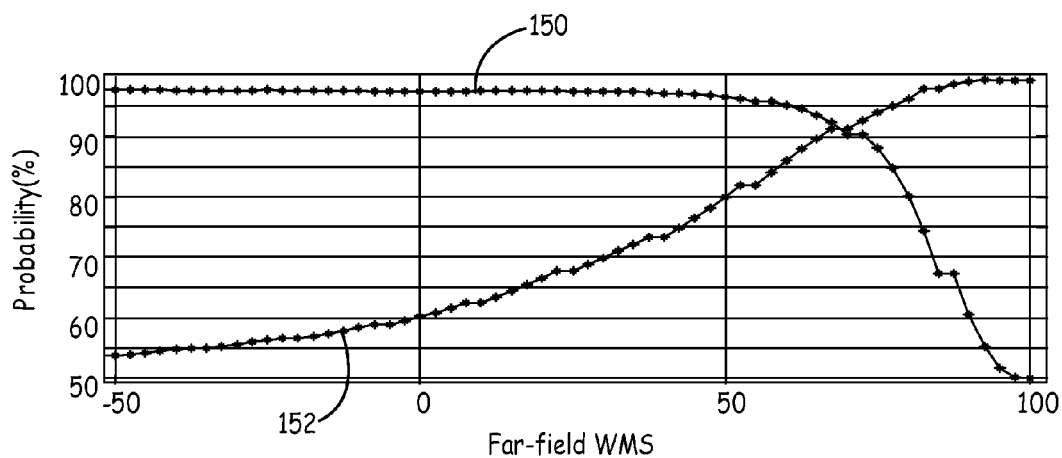
FIGS. 9-14 are graphs of probability curves for a number of beat morphology parameters.

FIG. 9 is a graph of probability curves associated with far-field EGM wavelet matching scores (WMS). WMS are obtained by comparing wavelets of the EGMs of the beats in the database with wavelets of an EGM of a template beat. The comparison results in a WMS, which in the example illustrated in FIG. 9 ranges from −50 to 150. Probability curve 150 represents the probability that the beat of interest corresponds to a VT/VF beat as a function of the far-field WMS. Probability curve 150 may be obtained, for example, by computing $P_{VT/VF}$ in accordance with equation (2) while varying the far-field WMS threshold from −50 to 100, where X is the number of VT/VF beats of the database that are less than or equal to $T_d$, Y is the number of SVT beats of the database that are less than or equal to $T_d$, and $T_d$ is the far-field WMS threshold in this example.

Probability curve 152 represents the probability that the beat of interest corresponds to a SVT beat as a function of the WMS. Probability curve 152 may be obtained, for example, by computing $P_{SVT}$ in accordance with equation (3) while varying the WMS from −50 to 100, where X is the number of VT/VF beats of the database that are greater than or equal to $T_d$, Y is the number of SVT beats of the database that are greater than or equal to $T_d$ and $T_d$ is the far-field WMS threshold.

Probability curves 150 and 152 cross at a WMS of approximately 70, which the IMD may use as a nominal threshold for FF WMS. Processor 70 may use probability curves 150 and 152, equations estimating probability curves 150 and 152, or a chart corresponding to probability curves 150 and 152, to determine the probability that the beat is a VT/VF beat and the probability that the beat is an SVT beat, respectively, based solely on a WMS of a far-field EGM associated with the beat of interest.

Figure 10:
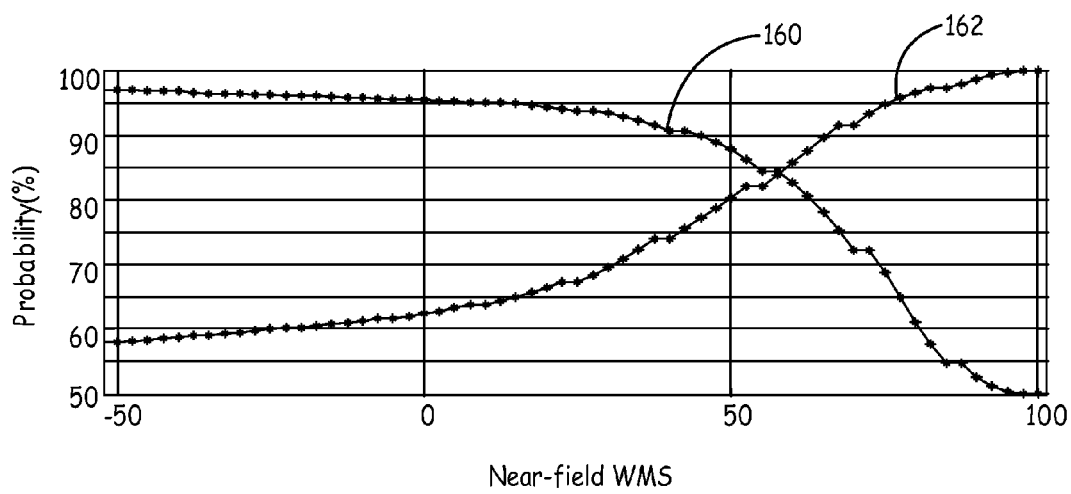

FIG. 10 is a graph of probability curves associated with near-field EGM wavelet matching scores (WMS). The near-field WMS are obtained in the same manner as the far-field WMS, except wavelets of the near-field EGMs are used instead of far-field EGMs. Probability curve 160 represents the probability that the beat of interest corresponds to a VT/VF beat as a function of the near-field WMS. Probability curve 160 may be obtained, for example, by computing $P_{VT/VF}$ in accordance with equation (2) while varying the near-field WMS threshold from −50 to 100, where X is the number of VT/VF beats of the database that are less than or equal to $T_d$, Y is the number of SVT beats of the database that are less than or equal to $T_d$ and $T_d$ is the near-field WMS threshold.

Probability curve 162 represents the probability that the beat of interest corresponds to a SVT beat as a function of the near-field WMS. Probability curve 162 may be obtained, for example, by computing $P_{SVT}$ in accordance with equation (3) while varying the WMS from −50 to 100, where X is the number of VT/VF beats of the database that are greater than or equal to $T_d$, Y is the number of SVT beats of the database that are greater than or equal to $T_d$ and $T_d$ is the near-field WMS threshold.

Probability curves 160 and 162 cross at a near-field WMS of approximately 60, which the IMD may use as a nominal threshold for the near-field WMS. Processor 70 may use probability curves 160 and 162, equations estimating probability curves 160 and 162, or a chart corresponding to probability curves 160 and 162, to determine the probability that the beat is a VT/VF beat and the probability that the beat is an SVT beat, respectively, based solely on a WMS of a near-field EGM associated with the beat of interest.

Figure 11:
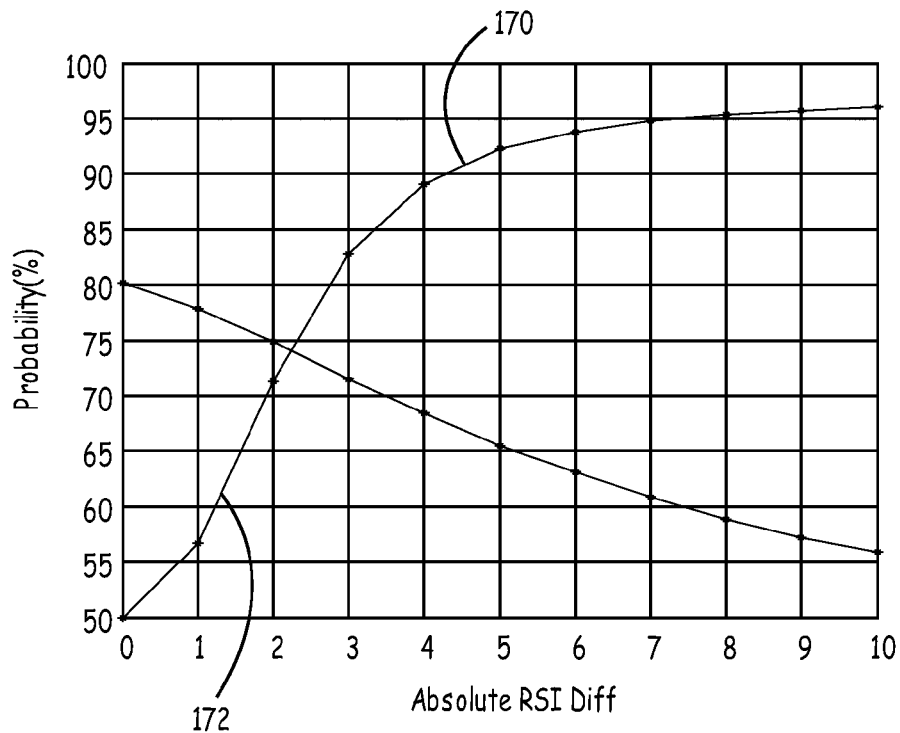

FIG. 11 is a graph of probability curves associated with the RSI beat morphology parameter. In particular, the probability curves are associated with the absolute value of the difference between the RSI value of a beat of interest and the RSI value of a template beat. Probability curve 170 represents the probability that the beat of interest is indicative of VT/VF based on the absolute value of the difference of the RSI of the beat of interest and the RSI of the template beat. A large difference in RSI values between the beat of interest and the template may be indicative of VT/VF. Probability curve 170 may be obtained, for example, by computing $P_{VT/VF}$ in accordance with equation (2) while varying the RSI difference threshold, e.g., from 0 to 10 in the case of FIG. 11, with X being the number of VT/VF beats of the database that are greater than or equal to $T_d$, Y being the number of SVT beats of the database that are greater than or equal to $T_d$ and $T_d$ being the RSI difference threshold.

Probability curve 172 represents the probability that the beat of interest is indicative of SVT based on the absolute value of the difference of the RSI of the beat of interest and the RSI of the template beat. Probability curve 172 may be obtained, for example, by computing $P_{SVT}$ in accordance with equation (3) while varying the RSI difference threshold, e.g., from 0 to 10 in the case of FIG. 11, with X being the number of VT/VF beats of the database that are less than or equal to $T_d$, Y being the number of SVT beats of the database that are less than or equal to $T_d$ and $T_d$ being the RSI difference threshold.

Probability curves 170 and 172 cross at a RSI difference of approximately 2.3. Processor 70 may use probability curves 170 and 172, equations estimating probability curves 170 and 172, or a chart corresponding to probability curves 170 and 172, to determine the probability that the beat is a VT/VF beat and the probability that the beat is an SVT beat, respectively, based solely on the RSI difference between the beat of interest and the template beat.

Figure 12:
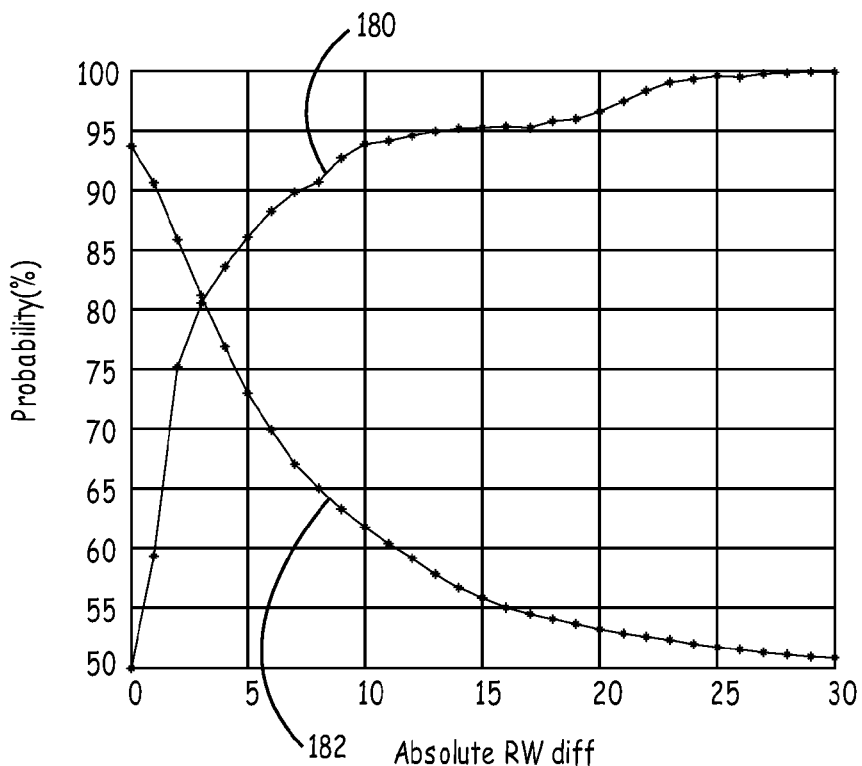

FIG. 12 is a graph of probability curves associated with the RW beat morphology parameter. In particular, the probability curves are associated with the absolute value of the difference between the RW value of a beat of interest and the RW value of a template beat. Probability curve 180 represents the probability that the beat of interest is indicative of VT/VF based on the absolute value of the difference of the RW value of the beat of interest and the RW value of the template beat. A large difference in RW values between the beat of interest and the template may be indicative of VT/VF. Probability curve 180 may be obtained, for example, by computing $P_{VT/VF}$ in accordance with equation (2) while varying the RW difference threshold, e.g., from 0 to 30 in the case of FIG. 12, with X being the number of VT/VF beats of the database that are greater than or equal to $T_d$, Y being the number of SVT beats of the database that are greater than or equal to $T_d$ and $T_d$ being the RW difference threshold.

Probability curve 182 represents the probability that the beat of interest is indicative of SVT based on the absolute value of the difference of the RW value of the beat of interest and the RW value of the template beat. Probability curve 182 may be obtained, for example, by computing $P_{SVT}$ in accordance with equation (3) while varying the RW difference threshold, e.g., from 0 to 30 in the case of FIG. 12, with X being the number of VT/VF beats of the database that are less than or equal to $T_d$, Y being the number of SVT beats of the database that are less than or equal to $T_d$ and $T_d$ being the RW difference threshold.

Probability curves 180 and 182 cross at a RW difference of approximately 3. Processor 70 may use probability curves 180 and 182, equations estimating probability curves 180 and 182, or a chart corresponding to probability curves 180 and 182, to determine the probability that the beat is a VT/VF beat and the probability that the beat is an SVT beat, respectively, based solely on the RW difference between the beat of interest and the template beat.

Figure 13:
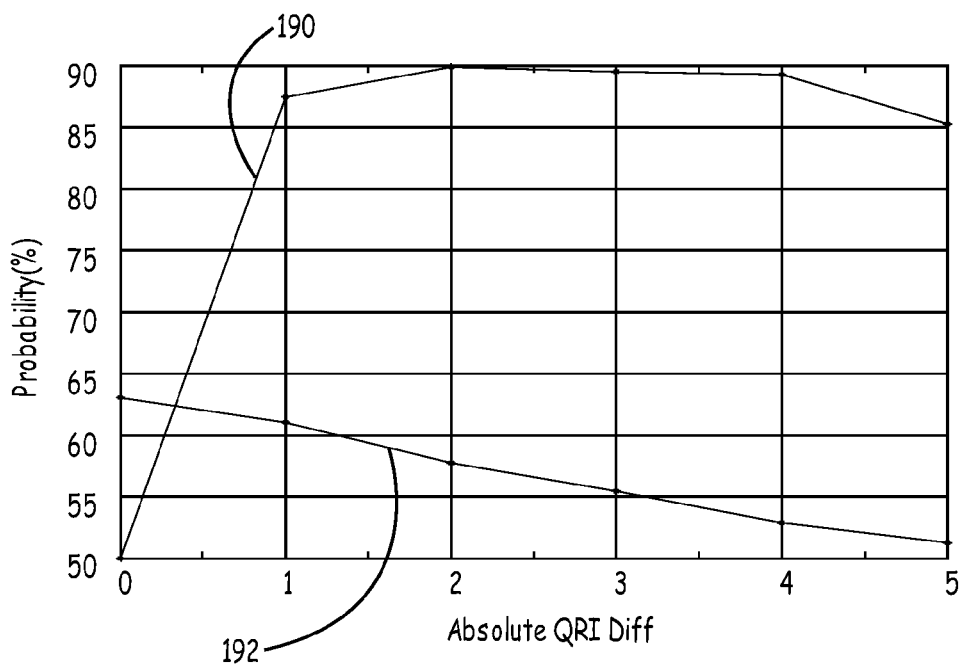

FIG. 13 is a graph of probability curves associated with the QRI beat morphology parameter. In particular, the probability curves are associated with the absolute value of the difference between the QRI value of a beat of interest and the QRI value of a template beat. Probability curve 190 represents the probability that the beat of interest is indicative of VT/VF based on the absolute value of the difference of the QRI value of the beat of interest and the QRI value of the template beat. A large difference in QRI values between the beat of interest and the template may be indicative of VT/VF. Probability curve 190 may be obtained, for example, by computing $P_{VT/VF}$ in accordance with equation (2) while varying the QRI difference threshold, e.g., from 0 to 5 in the case of FIG. 13, with X being the number of VT/VF beats of the database that are greater than or equal to $T_d$, Y being the number of SVT beats of the database that are greater than or equal to $T_d$ and $T_d$ being the QRI difference threshold.

Probability curve 192 represents the probability that the beat of interest is indicative of SVT based on the absolute value of the difference of the QRI value of the beat of interest and the QRI value of the template beat. Probability curve 192 may be obtained, for example, by computing $P_{SVT}$ in accordance with equation (3) while varying the QRI difference threshold, e.g., from 0 to 5 in the case of FIG. 13, with X being the number of VT/VF beats of the database that are less than or equal to $T_d$, Y being the number of SVT beats of the database that are less than or equal to $T_d$ and $T_d$ being the QRI difference threshold.

Probability curves 190 and 192 cross at a QRI difference of approximately 0.7. Processor 70 may use probability curves 190 and 192, equations estimating probability curves 190 and 192, or a chart corresponding to probability curves 190 and 192, to determine the probability that the beat is a VT/VF beat and the probability that the beat is an SVT beat, respectively, based solely on the QRI difference between the beat of interest and the template beat. For the cases of developing new Q wave (relative to template without Q wave), the VT/VF probability is 87.48%. In addition, analysis showed that, for the cases losing Q wave (relative to template with Q wave), the VT/VF probability is 68.44%.

Figure 14:
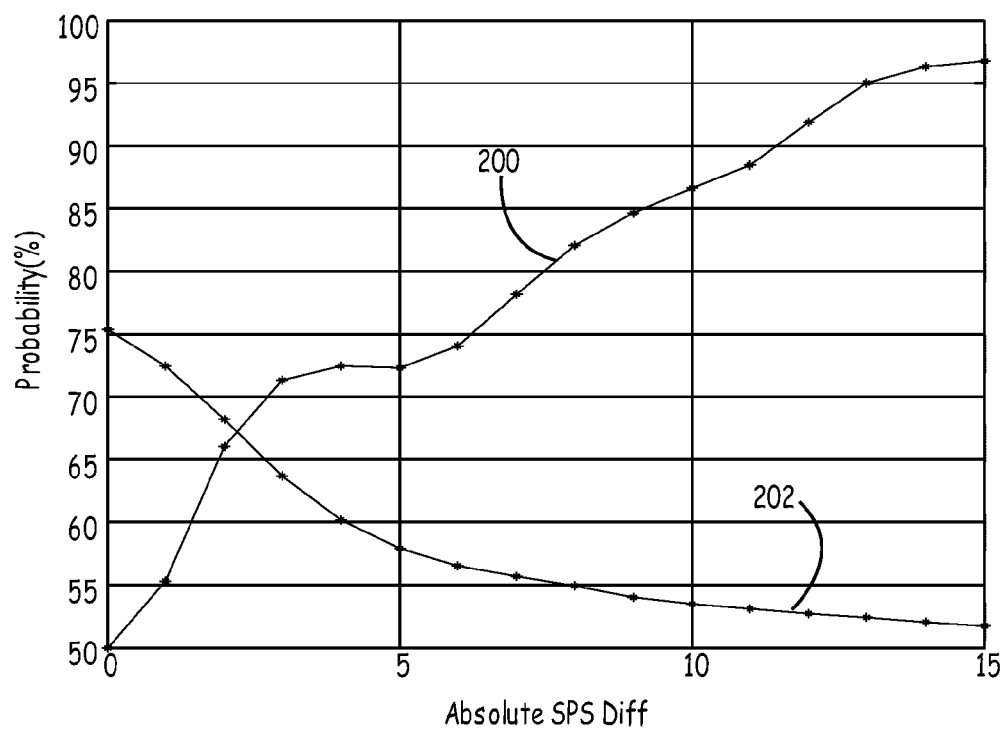

FIG. 14 is a graph of probability curves associated with the SPS beat morphology parameter. In particular, the probability curves are associated with the absolute value of the difference between the SPS value of a beat of interest and the SPS value of a template beat. Probability curve 200 represents the probability that the beat of interest is indicative of VT/VF based on the absolute value of the difference of the SPS value of the beat of interest and the SPS value of the template beat. Probability curve 200 may be obtained, for example, by computing $P_{VT/VF}$ in accordance with equation (2) while varying the SPS difference threshold, e.g., from 0 to 15 in the example of FIG. 14, with X being the number of VT/VF beats of the database that are greater than or equal to $T_d$, Y being the number of SVT beats of the database that are greater than or equal to $T_d$ and $T_d$ being the SPS difference threshold.

Probability curve 202 represents the probability that the beat of interest is indicative of SVT based on the absolute value of the difference of the SPS value of the beat of interest and the SPS value of the template beat. Probability curve 202 may be obtained, for example, by computing $P_{SVT}$ in accordance with equation (3) while varying the SPS difference threshold, e.g., from 0 to 15 in the case of FIG. 14, with X being the number of VT/VF beats of the database that are less than or equal to $T_d$, Y being the number of SVT beats of the database that are less than or equal to $T_d$ and $T_d$ being the SPS difference threshold.

Probability curves 200 and 202 cross at a SPS difference of approximately 2.3. Processor 70 may use probability curves 200 and 202, equations estimating probability curves 200 and 202, or a chart corresponding to probability curves 200 and 202, to determine the probability that the beat is a VT/VF beat and the probability that the beat is an SVT beat, respectively, based solely on the SPS difference between the beat of interest and the template beat.

FIGS. 9-14 illustrate example probability curves that define the discrimination power of each morphology parameter separately. The correlation between each parameter and all the other parameters for the example morphology parameters is provided in Table 1. Processor 70 may use all or a portion of these parameters to determine the independent contribution coefficient (i.e., the weight) to attribute to each parameter individually.

TABLE 1

Correlation between parameters

| Parameters | Correlation Coefficient (Absolute Value) |
|---|---|
| FFWMS vs. NFWMS | 0.51 |
| FFWMS vs. RW | 0.57 |
| FFWMS vs. RSI | 0.50 |
| FFWMS vs. QRI | 0.46 |
| FFWMS vs. SPS | 0.32 |
| FFWMS vs. RPC | 0.53 |
| NFWMS vs. RW | 0.43 |
| NFWMS vs. RSI | 0.35 |
| NFWMS vs. QRI | 0.28 |
| NFWMS vs. SPS | 0.37 |
| NFWMS vs. RPC | 0.47 |
| RW vs. RSI | 0.26 |
| RW vs. QRI | 0.23 |
| RW vs. SPS | 0.36 |
| RW vs. RPC | 0.34 |
| RSI vs. QRI | 0.34 |
| RSI vs. SPS | 0.19 |
| RSI vs. RPC | 0.39 |
| QRI vs. SPS | 0.09 |
| QRI vs. RPC | 0.41 |
| SPS vs. RPC | 0.24 |

After obtaining the parameters associated with the rhythm, processor 70 may compare the parameters to the corresponding parameters of the template rhythm to determine absolute difference values between the parameters. Processor 70 may use the probability curves of FIGS. 9-14 or equations or charts estimating the probability curves to determine the probability that the rhythm is treatable (VT/VF) beat and the probability that the rhythm is non-treatable (SVT) based on each of the individual parameters separately. Processor 70 also obtains an independent contribution coefficient associated with each of parameters based on the correlations among the parameters, e.g., the correlation coefficients provided in Table 1.

Processor 70 uses the obtained probabilities and independent contribution coefficients to compute an overall probability P that the condition exists in accordance with the equation below:

$$P = \sum_{i=0}^{n} w_i * p_i, \quad (4)$$

where $w_i$ is the independent contribution coefficient of the $i^{th}$ parameter, $p_i$ is the probability of the $i^{th}$ parameter and n is equal to the number of parameters. In particular, processor 70 multiplies each of the probabilities associated with the individual parameters by the corresponding independent contribution coefficient to obtain weighted probabilities for each morphological parameter and sums the weighted probabilities to obtain the overall probability P. Processor 70 computes the overall probability that the rhythm is treatable $P_{VT/VF}$ and the overall probability that the rhythm is non-treatable $P_{SVT}$ and determines whether or not the rhythm is treatable based on one or both of the overall probabilities as described herein.

Figure 15:
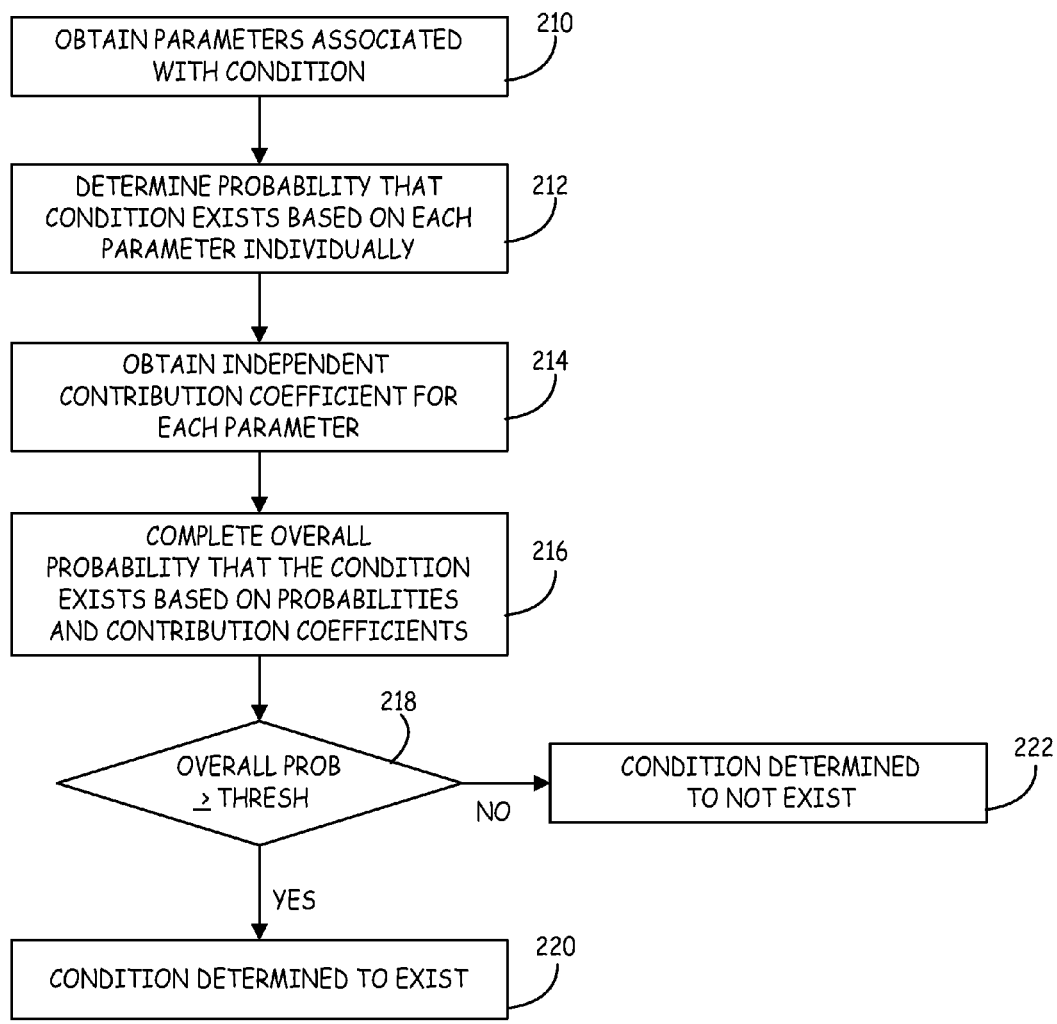
FIG. 15 is a flow diagram illustrating example operation of an IMD determining whether a condition exists in a patient in accordance with one aspect of this disclosure.

FIG. 15 is a flow diagram illustrating example operation of processor 70 determining whether a condition exists in a patient in accordance with one aspect of this disclosure. Processor 70 obtains parameters associated with a condition of patient 12 (210). For example, processor 70 may analyze sensed cardiac signals to obtain parameters that characterize a rhythm of heart 18 of patient 12. In some instances, the parameters that characterize the rhythm may include a far-field WMS, near-field WMS, R-wave symmetry index (RSI), R-wave width (RW), Q-wave R-wave index (QRI), R-wave polarity code (RPC), and slope peak shift (SPS). In other instances, the parameters may include a low slope content (LSC), normalized mean rectified amplitude (NMRA) spectral width (SW), or signal overall variability. Moreover, other non-morphology parameters may also be used such as heart rate, intracardiac or intravascular pressure, oxygen saturation, blood pressure, blood flow or the like.

Processor 70 determines a probability that the condition exists for each of the parameters individually (212). Processor 70 may obtain the probabilities for each of the parameters using the probability curves of FIGS. 9-14, or equations or charts that approximate the probability curves. Each of the probabilities represent the likelihood that the condition exists based solely on the particular, corresponding morphological parameter. In instances in which the probability curve corresponds with a difference between the parameters of the rhythm and the corresponding parameter of a template rhythm, processor 70 may compute such a difference.

Processor 70 obtains an independent contribution coefficient associated with each of parameters (214). The independent contribution coefficient represents the independent contribution of the particular morphological parameter to the overall probability that the condition exists. The independent contribution coefficient is computed based on the correlation coefficients among the various parameters. If processor 70 analyzes three morphological parameters x1, x2 and x3, for example, the independent contribution coefficient for each of the morphological parameters are w1=(2−c12−c13), w2=(2−c12−c23) and w3=(2−c13−c23), respectively, where c12 is the correlation between x1 and x2, c23 is the correlation between x2 and x3 and c13 is the correlation between x1 and x3.

Processor 70 computes an overall probability P that the condition exists based on the obtained probabilities and independent contribution coefficients (216). In particular, processor 70 multiplies each of the probabilities associated with the individual parameters by the corresponding independent contribution coefficient to obtain weighted probabilities for each morphological parameter and sums the weighted probabilities to obtain the overall probability P.

Processor 70 compares the overall probability that the condition exists to a threshold value (218). If the overall probability that the condition exists is greater than or equal to the threshold value (the "YES" branch of 218), processor 70 determines that the condition exists (220). If the overall probability that the condition exists is less than the threshold value (the "NO" branch of 218), processor 70 determines that the condition does not exist (222).

Figure 16:
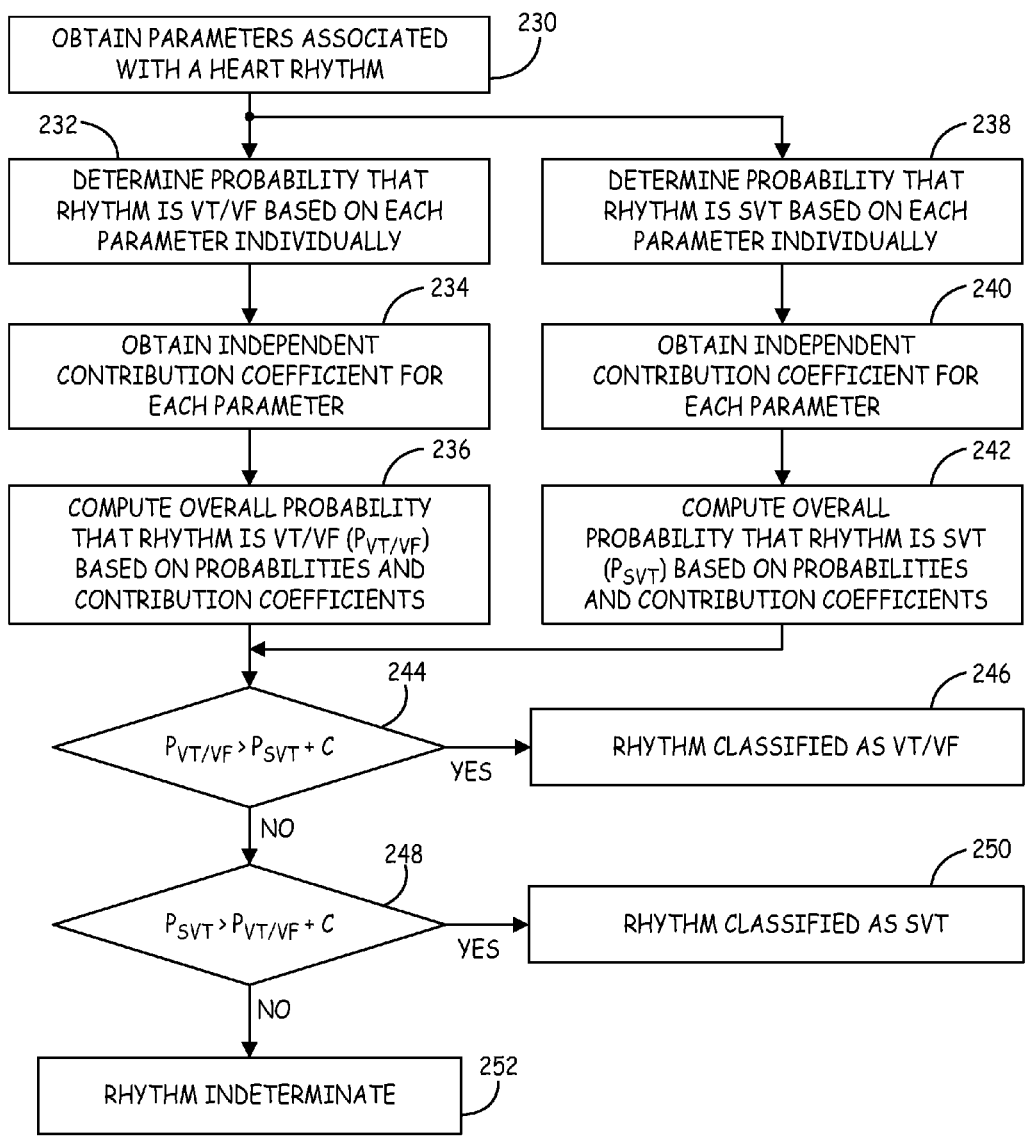
FIG. 16 is a flow diagram illustrating example operation of an IMD determining whether a rhythm is treatable in accordance with another aspect of this disclosure.

FIG. 16 is a flow diagram illustrating example operation of processor 70 determining whether a rhythm is treatable (VT/VF) in accordance with one aspect of this disclosure. Processor 70 obtains parameters associated with a heart rhythm of patient 12 (230). For example, the parameters that characterize the rhythm may include a far-field WMS, near-field WMS, R-wave symmetry index (RSI), R-wave width (RW), Q-wave R-wave index (QRI), R-wave polarity code (RPC), and slope peak shift (SPS). In another example, the parameters may include a low slope content (LSC), normalized mean rectified amplitude (NMRA) spectral width (SW), or signal overall variability.

Processor 70 determines a probability that the rhythm is VT/VF for each of the parameters individually (232). Processor 70 may obtain the probabilities for each of the parameters using the VT/VF probability curves of FIGS. 9-14, or equations or charts that approximate the VT/VF probability curves. Each of the probabilities represents the likelihood that the rhythm is VT/VF based solely on the particular morphological parameter. In instances in which the probability curve corresponds with a difference between the parameters of the rhythm and the corresponding parameter of a template rhythm, processor 70 may compute such a difference and use the difference to determine the probability.

Processor 70 obtains an independent contribution coefficient associated with each of parameters (234). The independent contribution coefficient represents the independent contribution of the particular morphological parameter to the overall probability that the condition exists. Processor 70 computes an overall probability that the rhythm is VT/VF ($P_{VT/VF}$) based on the obtained probabilities and independent contribution coefficients (236). In particular, processor 70 multiplies each of the probabilities associated with the individual parameters by the corresponding independent contribution coefficient to obtain weighted probabilities for each morphological parameter and sums the weighted probabilities to obtain the overall probability $P_{VT/VF}$.

Processor 70 also determines a probability that the rhythm is SVT for each of the parameters individually (238). Processor 70 may obtain the probabilities for each of the parameters using the SVT probability curves of FIGS. 9-14, or equations or charts that approximate the SVT probability curves. Each of the probabilities represents the likelihood that the rhythm is SVT based solely on the particular morphological parameter. In instances in which the probability curve corresponds with a difference between the parameters of the rhythm and the corresponding parameter of a template rhythm, processor 70 may compute such a difference and use the difference to determine the probability.

Processor 70 obtains an independent contribution coefficient associated with each of parameters (240). The independent contribution coefficient represents the independent contribution of the particular morphological parameter to the overall probability that the condition exists. Processor 70 computes an overall probability that the rhythm is SVT ($P_{SVT}$) based on the obtained probabilities and independent contribution coefficients (242). In particular, processor 70 multiplies each of the probabilities associated with the individual parameters by the corresponding independent contribution coefficient to obtain weighted probabilities for each morphological parameter and sums the weighted probabilities to obtain the overall probability $P_{SVT}$.

Processor 70 determines whether $P_{VT/VF}$ is greater than or equal to $P_{SVT}+C$ (244). If $P_{VT/VF}$ is greater than or equal to $P_{SVT}+C$ ("YES" branch of 244), processor 70 classifies the rhythm as VT/VF (246). If $P_{VT/VF}$ is less than $P_{SVT}+C$ ("NO" branch of 244), processor 70 determines whether $P_{SVT}$ is greater than ore equal to $P_{VT/VF}+C$ (248). If $P_{SVT}$ is greater than or equal to $P_{VT/VF}+C$ ("YES" branch of 248), processor 70 classifies the rhythm as SVT (250). If $P_{SVT}$ is less than $P_{VT/VF}+C$ ("NO" branch of 248), processor 70 determines that the rhythm is indeterminate (252). As described in detail above, processor 70 may control stimulation module 74 to deliver therapy to heart 18 based upon the classification of the rhythm. If the rhythm is determined to be non-treatable (SVT), stimulation module 74 does not deliver electrical stimulation to the ventricles. If the rhythm is determined to be treatable (VT/VF), however, stimulation module 74 delivers ventricular stimulation therapy, e.g., in the form of ATP, cardioversion shock(s), defibrillation shock(s) or a combination thereof.

The techniques described in this disclosure, including those attributed to ICD 16 or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete digital, analog or logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. However, these examples should not be considered limiting of the techniques as described herein. Although this disclosure is mainly described in the context of detecting whether an arrhythmia is shockable or non-shockable, the techniques of this disclosure may be used to integrate multiple parameters together to determine whether other conditions of a patient exist based on determined probabilities associated with the parameters and correlations between each of the parameters. For example, such techniques may be used for heart failure monitoring, cardiac ischemia detection, discriminating extra-cardiac noise from true cardiac signals, epilepsy monitoring and control, non-invasive risk stratification, medical diagnostic testing, patient wellness monitoring, or in other cardiac or non-cardiac contexts. These and other examples are within the scope of the following claims.

The invention claimed is:
1. A method comprising:
obtaining a plurality of parameters associated with a rhythm of a heart of a patient;
obtaining probabilities that the rhythm is indicative of one of ventricular tachycardia (VT) or ventricular fibrillation (VF) based on each of the plurality of parameters individually;
obtaining correlations between each of the parameters and other remaining ones of the plurality of parameters; and
determining whether the rhythm is indicative of one of VT or VF based at least on the probabilities and correlations wherein determining whether the rhythm is indicative of one of VT or VF based on the probabilities and correlations comprises:
  obtaining independent contribution coefficients associated with each of parameters using the correlations, wherein the independent contribution coefficients represent the independent contribution of the particular parameter to the overall probability that the rhythm is indicative of one of VT or VF;
  determining an overall probability that the rhythm is treatable by multiplying each of the probabilities by the corresponding one of the independent contribution coefficients to obtain weighted probabilities and summing the weighted probabilities;
  determining whether the rhythm is indicative of one of VT or VF based at least on the overall probability that the rhythm is indicative of one of VT or VF.

2. The method of claim 1, wherein determining whether the rhythm is indicative of one of VT or VF based at least on the overall probability that the rhythm is indicative of one of VT or VF comprises:
  comparing the overall probability that the rhythm is indicative of one of VT or VF to a threshold probability value; and
  determining that the rhythm is indicative of one of VT or VF when the overall probability is greater than or equal to the threshold probability value.

3. The method of claim 1, further comprising:
  obtaining probabilities that the rhythm is indicative of a supra-ventricular tachycardia (SVT) based on each of the plurality of parameters individually;
  obtaining independent contribution coefficients associated with each of parameters that represent the independent contribution of the particular parameter to the overall probability that the rhythm is indicative of SVT;
  determining an overall probability that the rhythm is indicative of SVT by multiplying each of the probabilities by the corresponding one of the independent contribution coefficients to obtain weighted probabilities and summing the weighted probabilities; and
  determining whether the rhythm is indicative of one of VT or VF based on the overall probability that the rhythm is indicative of one of VT or VF and the overall probability that the rhythm is indicative of SVT.

4. The method of claim 3, wherein determining whether the rhythm is indicative of one of VT or VF based on the overall probability that the rhythm is indicative of one of VT or VF and the overall probability that the rhythm is indicative of SVT comprises:
  determining that the rhythm is indicative of one of VT or VF when the overall probability that the rhythm is indicative of one of VT or VF is greater than the overall probability that the rhythm is indicative of SVT plus a constant;
  determining that the rhythm is indicative of SVT when the overall probability that the rhythm is indicative of SVT is greater than the overall probability that the rhythm is indicative of one of VT or VF plus the constant; and
  determining that the rhythm is indeterminate when neither of the conditions are met.

5. The method of claim 1, further comprising:
  delivering a therapy to at least one ventricle of the heart of the patient when the rhythm is determined to be indicative of one of VT or VF; and
  withholding therapy to either ventricles of the patient when the rhythm is determined to be indicative of SVT.

6. The method of claim 1, wherein the plurality of parameters associated with the rhythm include two or more of a far-field wavelet matching score (WMS), a near-field WMS, an R-wave symmetry index (RSI), a R-wave width (RW), a Q-R index (QRI), a R-wave polarity code (RPC), a slope peak shift (SPS), a low slope content (LSC), a normalized mean rectified amplitude (NMRA), a spectral width (SW), and a signal overall variability (SOV).

7. An implantable medical device comprising:
  a sensing module configured to acquire cardiac signals associated with electrical activity of a heart of a patient via at least one sensor; and
  a processor configured to analyze the acquired cardiac signals to obtain a plurality of parameters associated with a rhythm of a heart of a patient, to obtain probabilities that the rhythm is indicative of one of ventricular tachycardia (VT) or ventricular fibrillation (VF) based on each of the plurality of parameters individually, and to determine whether the rhythm is indicative of one of VT or VF based at least on the obtained probabilities and correlations wherein the processor is configured to obtain independent contribution coefficients associated with each of parameters using the correlations, wherein the independent contribution coefficients represent the independent contribution of the particular parameter to the overall probability that the rhythm is indicative of one of VT or VF, to determine an overall probability that the rhythm is indicative of one of VT or VF by multiplying each of the probabilities by the corresponding one of the independent contribution coefficients to obtain weighted probabilities and summing the weighted probabilities, and to determine whether the rhythm is indicative of one of VT or VF based at least on the overall probability that the rhythm is indicative of one of VT or VF.

8. The device of claim 7, wherein the processor is configured to compare the overall probability that the rhythm is indicative of one of VT or VF to a threshold value and to determine that the rhythm is indicative of one of VT or VF when the overall probability is greater than or equal to the threshold probability.

9. The device of claim 7, wherein the processor is configured to obtain probabilities that the rhythm is indicative of a supra-ventricular tachycardia (SVT) based on each of the plurality of parameters individually, to obtain independent contribution coefficients associated with each of parameters that represent the independent contribution of the particular parameter to the overall probability that the rhythm is indicative of SVT, to determine an overall probability that the rhythm is indicative of SVT by multiplying each of the probabilities by the corresponding one of the independent contribution coefficients to obtain weighted probabilities and summing the weighted probabilities, and to determine whether the rhythm is indicative of one of VT or VF based on the overall probability that the rhythm is indicative of one of VT or VF and the overall probability that the rhythm is indicative of SVT.

10. The device of claim 9, wherein the processor is configured to determine that the rhythm is indicative of one of VT or VF when the overall probability that the rhythm is indicative of one of VT or VF is greater than the overall probability that the rhythm is indicative of SVT plus a constant, to determine that the rhythm is indicative of SVT when the overall probability that the rhythm is indicative of SVT is greater than the overall probability that the rhythm is indicative of one of VT or VF plus the constant, and to determine that the rhythm is indeterminate when neither of the conditions are met.

11. The device of claim 7, further comprising a stimulation module configured to deliver cardiac electrical stimulation therapy to the patient, wherein the processor is configured to control the stimulation therapy module to deliver electrical stimulation therapy to at least one ventricle of the heart of the patient when the rhythm is determined to be indicative of one of VT or VF and to withhold delivery of electrical stimulation therapy to either ventricles of the patient when the rhythm is determined to be indicative of SVT.

12. The device of claim 7, wherein the plurality of parameters associated with the rhythm include two or more of a far-field wavelet matching score (WMS), a near-field WMS, an R-wave symmetry index (RSI), a R-wave width (RW), a Q-R index (QRI), a R-wave polarity code (RPC), a slope peak shift (SPS), a low slope content (LSC), a normalized mean rectified amplitude (NMRA), a spectral width (SW), and a signal overall variability (SOV).

13. The device of claim 7, wherein at least one of the parameters comprises a parameter associated with an electrogram (EGM) of the patient and at least one of the parameters comprises information sensed by at least one hemodynamic sensor.

14. A non-transitory computer-readable storage medium comprising instructions that, when executed by a processor in an implantable medical device, cause the processor to:
obtain a plurality of parameters associated with a rhythm of a heart of a patient;
obtain probabilities that the rhythm is indicative of one of ventricular tachycardia (VT) or ventricular fibrillation (VF) based on each of the plurality of parameters individually;
obtain correlations between each of the parameters and other remaining ones of the plurality of parameters;
obtain independent contribution coefficients associated with each of parameters using the correlations, wherein the independent contribution coefficients represent the independent contribution of the particular parameter to the overall probability that the rhythm is indicative of one of VT or VF;
determine an overall probability that the rhythm is indicative of one of VT or VF by multiplying each of the probabilities by the corresponding one of the independent contribution coefficients to obtain weighted probabilities and summing the weighted probabilities; and
determine whether the rhythm is indicative of one of VT or VF based at least on the overall probability that the rhythm is indicative of one of VT or VF.

15. The non-transitory computer-readable storage medium of claim 14, wherein the instructions that cause the processor to determine whether the rhythm is indicative of one of VT or VF based at least on the overall probability that the rhythm is indicative of one of VT or VF comprise instructions that, when executed, cause the processor to:
compare the overall probability that the rhythm is indicative of one of VT or VF to a threshold value; and
determine that the rhythm is indicative of one of VT or VF when the overall probability is greater than or equal to the threshold probability.

16. The non-transitory computer-readable storage medium of claim 14, wherein the instructions that cause the processor to determine whether the rhythm is indicative of one of VT or VF based at least on the overall probability that the rhythm is indicative of one of VT or VF comprise instructions that, when executed, cause the processor to:
obtain probabilities that the rhythm is indicative of a supraventricular tachycardia (SVT) based on each of the plurality of parameters individually;
obtain independent contribution coefficients associated with each of parameters that represent the independent contribution of the particular parameter to the overall probability that the rhythm is indicative of SVT;
determine an overall probability that the rhythm is indicative of SVT by multiplying each of the probabilities by the corresponding one of the independent contribution coefficients to obtain weighted probabilities and summing the weighted probabilities; and
determine whether the rhythm is indicative of one of VT or VF based on the overall probability that the rhythm is indicative of one of VT or VF and the overall probability that the rhythm is indicative of SVT.

17. The non-transitory computer-readable storage medium of claim 16, wherein the instructions that cause the processor to determine whether the rhythm is indicative of one of VT or VF based on the overall probability that the rhythm is indicative of one of VT or VF and the overall probability that the rhythm is indicative of SVT comprise instructions that, when executed, cause the processor to:
determine that the rhythm is indicative of one of VT or VF when the overall probability that the rhythm is indicative of one of VT or VF is greater than the overall probability that the rhythm is indicative of SVT plus a constant;
determine that the rhythm is indicative of SVT when the overall probability that the rhythm is indicative of SVT is greater than the overall probability that the rhythm is indicative of one of VT or VF plus the constant; and
determine that the rhythm is indeterminate when neither of the conditions are met.

* * * * *